(12) United States Patent
Yodfat et al.

(10) Patent No.: US 8,491,529 B2
(45) Date of Patent: Jul. 23, 2013

(54) VENTED DISPENSING DEVICE AND METHOD

(75) Inventors: Ofer Yodfat, Maccabim-Reut (IL); Avraham Neta, Misgav (IL)

(73) Assignee: Medingo, Ltd., Yoqneam Illit (IL)

( * ) Notice: Subject to any disclaimer, the term of this patent is extended or adjusted under 35 U.S.C. 154(b) by 329 days.

(21) Appl. No.: 12/452,764

(22) PCT Filed: Jul. 20, 2008

(86) PCT No.: PCT/IL2008/001000
§ 371 (c)(1),
(2), (4) Date: Apr. 7, 2010

(87) PCT Pub. No.: WO2009/013735
PCT Pub. Date: Jan. 29, 2009

(65) Prior Publication Data
US 2010/0198187 A1 Aug. 5, 2010

Related U.S. Application Data

(60) Provisional application No. 60/961,528, filed on Jul. 20, 2007, provisional application No. 60/961,484, filed on Jul. 20, 2007, provisional application No. 60/961,382, filed on Jul. 20, 2007.

(51) Int. Cl.
*A61M 5/00* (2006.01)
(52) U.S. Cl.
USPC .................. 604/131; 604/890.1; 604/151
(58) Field of Classification Search
USPC ...................... 604/890.1, 131, 151
See application file for complete search history.

(56) References Cited

U.S. PATENT DOCUMENTS

| 3,631,847 A | 1/1972 | Hobbs, II |
| 3,770,607 A | 11/1973 | Williams |

(Continued)

FOREIGN PATENT DOCUMENTS

| CN | 2919644 Y | 7/2007 |
| WO | WO-2005082436 A1 | 9/2005 |

(Continued)

OTHER PUBLICATIONS

International Search Report for PCT Application No. PCT/IL2008/001000, mailed Dec. 10, 2008.

(Continued)

*Primary Examiner* — Laura Bouchelle
(74) *Attorney, Agent, or Firm* — Mintz Levin Cohn Ferris Glovsky and Popeo, P.C.

(57) ABSTRACT

Disclosed is a fluid dispensing device that includes at least one reservoir to hold the therapeutic fluid, at least one other unit requiring communication with ambient air, at least partly, to operate, and at least one housing defining an interior to retain the at least one reservoir and the at least one other unit. The at least one housing has at least one vent port formed on one or more of its walls. The at least one vent port is adapted to direct or communicate air to maintain pressure equilibrium between the air pressure in the interior of the at least one housing and the ambient air pressure outside the at least one housing, and provide communication with the ambient air to the at least one other unit requiring air to enable operation of the at least one other unit.

16 Claims, 17 Drawing Sheets

U.S. PATENT DOCUMENTS

| | | | |
|---|---|---|---|
| 3,771,694 A | | 11/1973 | Kaminski |
| 3,953,566 A | | 4/1976 | Gore |
| 4,030,495 A | * | 6/1977 | Virag .................... 604/123 |
| 4,194,041 A | | 3/1980 | Gore et al. |
| 4,313,439 A | | 2/1982 | Babb et al. |
| 4,429,000 A | | 1/1984 | Naka et al. |
| 4,498,843 A | | 2/1985 | Schneider et al. |
| 4,544,369 A | | 10/1985 | Skakoon et al. |
| 4,560,611 A | | 12/1985 | Naka et al. |
| 4,657,486 A | | 4/1987 | Stempfle et al. |
| 4,679,562 A | | 7/1987 | Luksha |
| 4,734,092 A | | 3/1988 | Millerd |
| 4,846,797 A | | 7/1989 | Howson et al. |
| 4,902,278 A | * | 2/1990 | Maget et al. .............. 604/132 |
| 5,352,513 A | | 10/1994 | Mrozinski et al. |
| 5,390,671 A | | 2/1995 | Lord et al. |
| 5,460,603 A | * | 10/1995 | DeSantis .................... 604/30 |
| 5,591,541 A | | 1/1997 | Oltman |
| 5,607,796 A | | 3/1997 | Jacus et al. |
| 5,658,356 A | | 8/1997 | Burns |
| 5,662,717 A | | 9/1997 | Burns |
| 5,688,864 A | | 11/1997 | Goodwin |
| 5,733,676 A | | 3/1998 | Dopp et al. |
| 5,804,327 A | | 9/1998 | Oltman |
| 5,904,998 A | | 5/1999 | Dopp et al. |
| 5,928,194 A | | 7/1999 | Maget |
| 5,938,640 A | * | 8/1999 | Maget et al. ............... 604/145 |
| 5,957,895 A | | 9/1999 | Sage et al. |
| 5,973,055 A | | 10/1999 | Michaud et al. |
| 5,985,475 A | | 11/1999 | Reynolds et al. |
| 6,143,164 A | | 11/2000 | Heller et al. |
| 6,485,461 B1 | | 11/2002 | Mason et al. |
| 6,589,229 B1 | | 7/2003 | Connelly et al. |
| 6,638,610 B1 | | 10/2003 | Yao |
| 6,676,993 B2 | | 1/2004 | Klare |
| 6,723,072 B2 | | 4/2004 | Flaherty et al. |
| 6,740,059 B2 | * | 5/2004 | Flaherty .................... 604/67 |
| 6,743,516 B2 | | 6/2004 | Murphy et al. |
| 6,811,884 B2 | | 11/2004 | Goodwin et al. |
| 6,854,603 B2 | | 2/2005 | Klare |
| 7,083,849 B1 | | 8/2006 | Albrecht et al. |
| 7,144,384 B2 | | 12/2006 | Gorman et al. |
| 2003/0161744 A1 | * | 8/2003 | Vilks et al. .................... 417/415 |
| 2005/0177108 A1 | | 8/2005 | Paul et al. |
| 2006/0184154 A1 | | 8/2006 | Moberg et al. |
| 2007/0073235 A1 | | 3/2007 | Estes et al. |
| 2007/0106218 A1 | | 5/2007 | Yodfat et al. |
| 2007/0191702 A1 | | 8/2007 | Yodfat et al. |
| 2007/0255198 A1 | | 11/2007 | Leong et al. |
| 2008/0051716 A1 | | 2/2008 | Stutz |
| 2008/0102119 A1 | | 5/2008 | Grovender et al. |
| 2008/0125701 A1 | | 5/2008 | Moberg et al. |
| 2008/0255516 A1 | | 10/2008 | Yodfat et al. |
| 2008/0269575 A1 | | 10/2008 | Iddan |
| 2008/0294142 A1 | | 11/2008 | Patel et al. |
| 2010/0121306 A1 | | 5/2010 | Yodfat et al. |
| 2010/0130932 A1 | | 5/2010 | Yodfat et al. |
| 2010/0191078 A1 | | 7/2010 | Yodfat et al. |
| 2010/0198187 A1 | | 8/2010 | Yodfat et al. |
| 2010/0217230 A1 | | 8/2010 | Yodfat et al. |
| 2010/0241086 A1 | | 9/2010 | Yodfat et al. |
| 2010/0298764 A1 | | 11/2010 | Yodfat et al. |

FOREIGN PATENT DOCUMENTS

| | | |
|---|---|---|
| WO | WO-2007037979 A2 | 4/2007 |
| WO | WO-2007045644 A1 | 4/2007 |
| WO | WO-2008139458 A2 | 11/2008 |
| WO | WO-2009125398 A2 | 10/2009 |

OTHER PUBLICATIONS

Written Opinion for PCT Application No. PCT/IL2008/001000, mailed Dec. 10, 2008.

* cited by examiner

VENTED DISPENSING DEVICE AND METHOD

CROSS-REFERENCE TO RELATED APPLICATIONS

The present application is a 35 U.S.C. 371 national stage entry of PCT/IL2008/001000, which has an international filing date of 20 Jul. 2008 and claims priority to U.S. Provisional Patent Application Nos. 60/961,528, 60/961,484 and 60/961,382, all of which were filed in the U.S. Patent & Trademark Office on 20 Jul. 2007. The present application incorporates herein by reference the disclosure of each of the above-referenced applications in its entirety.

BACKGROUND OF THE INVENTION

1. Field of the Invention

Embodiments of the present disclosure relate generally to a system, a device and a method for sustained medical infusion of fluids and/or continuous monitoring of body analyte. In some embodiments, a portable infusion patch-like device is provided that is securable (e.g., adherable) to the skin and that optionally may also continuously and/or periodically monitor body analytes. In some embodiments, a multi-component fluid dispensing and/or bodily analytes monitoring device is described that includes one or more vents configured to, for example, direct air to, among other things, balance pressure differences between the pressure within and outside its interior by enabling air transfer through the device while preventing entrance of water and other liquids which could affect functioning of the device.

2. Background of Invention

Medical treatment of several illnesses requires, under some circumstances, continuous or periodical drug infusion into various body compartments, such as subcutaneous and intravenous injections. For example, diabetes mellitus patients require the administration of varying amounts of insulin throughout the day to control their blood glucose levels. In recent years, ambulatory portable insulin infusion pumps have emerged as a superior alternative to multiple daily injections of insulin by syringe. These pumps, which deliver insulin at continuous basal rates as well as in bolus volumes, were developed to liberate patients from repeated self-administered injections, and to allow them to maintain a near-normal daily routine. In another example, ambulatory pumps may be used to treat post surgery pain where the treatment regiment requires relief by continuous or periodic administration of medication (e.g., administration of opium derivatives). These drugs can be locally delivered to the subcutaneous tissue surrounding the incision scar while avoiding systemic side effects of oral or intravenous administered analgesics. Another application of ambulatory pumps includes use of the pumps in the treatment of cancer patients that require continuous/periodical delivery of chemotherapy medications via an open vein access port.

Several ambulatory insulin infusion devices are available on the market. The first generation of such devices included disposable syringe-type reservoir, piston and tubes, as described, for example, in U.S. Pat. Nos. 3,631,847, 3,771,694, 4,657,486 and 4,544,369, the contents of all of which are hereby incorporated by reference in their entireties.

A drawback of these devices is their relatively large sizes and weights, resulting by their physical configuration and the relatively large driving mechanisms, e.g., syringes and pistons. These relatively bulky devices have to be carried in patients' pockets or be attached to the patients' belts. Consequently, the fluid delivery tubes of those devices are relatively long, usually longer than 60 cm, to enable needle insertion in remote sites of the body. Such uncomfortable bulky fluid delivery devices each having a relatively long tube are disfavored by the majority of diabetic insulin users because these devices interfere with the patients' regular activities, such as sleeping, exercising, etc.

To avoid tubing limitations, a second generation of pumps has been developed. Second generation pumps include a housing having a bottom surface adapted for attachment to the user's skin, a reservoir disposed within the housing, and an injection needle adapted for fluid communication with the reservoir. These skin securable (e.g., adhereable) devices are generally discarded every 2-3 days, much like the infusion sets employed in first generation pumps. Second generation devices are described, for example, in U.S. Pat. Nos. 5,957,895, 6,589,229 and 6,740,059, the contents of all of which are hereby incorporated by reference in their entireties. Other configurations of skin securable pumps are disclosed, for example, in U.S. Pat. Nos. 6,723,072 and 6,485,461, the contents of all of which are hereby incorporated by reference in their entireties. These patents describe, for example, a pump implemented as a single piece and remains secured to a user's skin for the entire usage duration. The needle emerges from the bottom surface of the device and is secured to the device housing. A drawback of these $2^{nd}$ generation devices is their relative bulkiness and their high cost of manufacture. Particularly, the reservoirs used in conjunctions with these devices are typically tubular and syringe-like, thus requiring a relatively large occupying space and relatively large physical dimensions (e.g., large thickness). Another drawback of second generation devices is that users have to discard the entire device, including expensive electronics and the driving mechanisms of the devices, every 2-3 days.

To avoid, for example, volume and cost constraints, $3^{rd}$ generation skin-secured devices have been proposed, as described, for example, in commonly-owned patent applications PCT/IL06/001276 and U.S. Ser. No. 11/397,115, filed Apr. 3, 2006, the contents of which are hereby incorporated by reference in their entireties. The device disclosed in these applications includes, in some embodiments, one or more of the following units:

1. A dispensing patch unit (hereinafter "dispensing patch", "patch" or "dispensing device")—the dispensing patch unit generally includes two parts, a disposable part and a reusable part. The reusable part comprises, for example, electronic components, including a motor, a buzzer and a controller. The electronic components are configured to control and monitor, for example, the activity of the dispensing patch. The buzzer is configured, for example, to alarm the user under certain circumstances (e.g., when the reservoir has been emptied). The disposable part comprises, for example, a reservoir for therapeutic fluid, a short delivery tube, an outlet port and an energy source (e.g., battery). In some embodiments, switches/buttons may be provided on the dispensing patch to allow for delivery of doses in response to manual commands. After connection of the reusable and disposable parts, the assembled device may form a sealed item that has a relatively thin dimension, thus rendering the whole device inexpensive, light and discrete.
2. A remote control unit, which can be used for data acquisition, programming, and communication of user inputs.
3. A cradle unit—a skin securable (e.g., adherable) structure that is attached to the skin and enables connection and disconnection of the dispensing patch unit.

4. A cannula cartridge—a unit that includes a cannula for delivering a therapeutic fluid into the patient body.

The dispensing patch unit may be attached to the body of a diabetic patient during the entire usage duration to achieve improved glycemic control. The two-part patch unit may be water tight to enable showering, swimming, and exposure to rain, food (e.g., soup) and beverages (e.g., beer, soda or coffee) that may unintentionally contaminate the device. Such two-part devices are described, for example, in co-owned U.S. Ser. No. 11/397,115 and in U.S. Provisional Application U.S. Ser. No. 60/922,794, entitled "Apparatus and method for pumping fluid into a mammal's body", filed Apr. 10, 2007, the contents of all which are hereby incorporated by reference in their entireties.

In some embodiments, a dispensing patch unit that includes a continuous analyte monitor (to enable insulin dispensing and glucose monitoring) may be used. Such a patch unit is described in commonly-owned pending U.S. patent application Ser. Nos. 11/706,606, filed Feb. 14, 2007, U.S. Provisional Application Nos. 60/842,869, filed Sep. 6, 2006 and 60/848,511, filed Sep. 29, 2006, the contents of all which are hereby incorporated by reference in their entireties. Such a dual-function patch unit may also be composed of two parts and may be controlled remotely or manually. Such a patch unit may be water tight as well.

SUMMARY OF THE INVENTION

Disclosed are vented fluid delivery devices and associated methods, in which one or more vents formed in the device cause the device to be impervious to fluids but pervious to one or more gases (e.g., oxygen). Such devices and methods may further be configured for example, to enable air (including) oxygen transfer to at least one unit of a fluid dispensing device that requires communication with ambient air, at least in part, to operate (e.g., a zinc-air battery). A vented fluid delivery device may also enable regulating pressure changes within the device as necessary to form an equilibrium with the pressure outside of the device, and/or enable increased transmission of sound waves created by components (e.g., alarms) within the device.

Some embodiments of the present disclosure are directed to a vented device that includes a water-tight and gas pervious, miniature, portable fluid dispensing unit. The vented device may include one or more vents disposed within at least one wall of at least one housing of the device. The fluid dispensing unit may be a patch type dispensing unit that is securable (e.g., adherable) to a patient's body and enables continuous and/or discrete controllable fluid delivery. In some embodiments, the delivered fluid is insulin. The dispensing patch unit may also include a fluid reservoir, a driving mechanism (e.g., a peristaltic pump or a piston), electronics (e.g., electronics included as part of a printed circuit board, or "PCB"), a power source and/or a delivery tube. In some embodiments, a audible notification unit (e.g., a buzzer) is provided to notify the patient under certain circumstances, e.g., when the reservoir is empty or is nearly empty. The power source may include one or more zinc-air batteries to supply the energy requirements of the dispensing patch including, for example, energy requirements of the pump's motor.

In some embodiments, the dispensing patch may comprise two parts: a reusable part and a disposable. The reusable part may include the relatively expensive components such as, for example, electronics (e.g., the electronics implementing the controller of the device) and a motor, while the disposable part may include the relatively less expensive components, including, for example, a fluid reservoir and a power source. In some embodiments, the dispensing patch may be sealed by at least one gasket or o-ring placed on the interface between the two parts (e.g., the reusable and disposable parts). Thus, a sealed compartment may be formed by attaching one part to the other. In some embodiments, an opening, also referred to as a vent or a vent port, may be provided in the housing of the dispensing patch so as to direct air to enable, for example, establishing pressure equilibrium within the interior of the device. The opening, or vent, may further enable air (including oxygen) transfer to one or more units of the device that require communication with ambient air, at least in part, to operate. Such one or more units may include zinc-air battery (ies). The opening (vent) may also be configured to direct air to enable air flow regulation (e.g., according to pressure changes) to perform pressure equilibration. The opening (vent) may also be configured to enable transmission of sound waves.

In some embodiments, a selective membrane covers the vent to prevent water from entering into the dispensing patch unit.

In some embodiments, the membrane allows a minimal rate of gas transfer that is at least 1 µl per hour.

In some embodiments, at least one vent is provided in a dispensing patch unit. In some embodiments, at least one vent is provided in a reusable part of the dispensing patch in the proximity of an audible notification module (e.g., a buzzer).

In some embodiments, at least one vent is provided in a disposable part of the dispensing patch in proximity of the reservoir.

In some embodiments, at least one vent is provided in the disposable part of the dispensing patch in proximity of a power source.

In some embodiments, a skin-securable (e.g., adherable) two-part dispensing patch unit is provided. After connection of the parts, the assembled patch unit is waterproof and at the same time pervious to oxygen.

In some embodiments, a water tight gas pervious housing for a dispensing patch unit is provided. In this type of a unit, the gas (e.g., oxygen) is consumed by at least one of the dispensing patch components. In some embodiments, a water tight, oxygen pervious housing for the dispensing patch unit is provided, in which the oxygen is consumed by at least one zinc air battery. In some embodiments, a water tight, oxygen pervious housing for dispensing patch unit is provided, in which the oxygen is consumed in the course of the occurrence of chemical reactions with glucose oxidase.

In some embodiments, a skin-securable (e.g., skin-adherable) infusion patch unit is provided that includes two sealed parts, reusable and disposable (i.e., each part is contained within its own sealed housing).

In some embodiments, a skin-securable (e.g., adherable) infusion patch unit is provided that includes two water tight parts, reusable and disposable, where one or both of the parts are pervious to at least one gas.

In some embodiments, a water tight, gas pervious housing for a dispensing patch unit is provided.

In some embodiments of the present disclosure, a fluid delivery device that includes a remote control unit and a dispensing patch unit configured for water tight sealing and at the same time gas permeability of one or more device housings is described. In some embodiments, an external, miniature, portable, programmable fluid dispensing patch unit that includes a vent that can be covered with a selectively permeable membrane is provided.

In some embodiments, a small, low cost, portable dispensing patch unit including disposable and reusable parts having a vent covered with a selectively permeable membrane is provided. The membrane is provided in one or more parts of the dispensing patch unit. The membrane may be protected by a perforated cover.

In some embodiments, a dispensing patch unit is provided that includes a sensor for measuring an analyte level (e.g., glucose level). The patch unit may be fitted with one or more housings that are water tight and gas pervious.

Some embodiments of the present disclosure include one or more housings for a fluid dispensing device, where the one or more housings include an aperture covered by a selectively permeable membrane made from a suitable material such as, for example, GORE-TEX™ and/or CELGARD™, configured to enable one or more gases to pass therethrough.

In some embodiments, in addition to being water proof, a skin-securable dispensing patch unit may be provided that enables air entry (venting) to enable performance of one or more of the following functions (applications):

To maintain pressure equilibrium between the interior of the patch unit and ambient atmosphere. Pressure differences between the patch unit interior and the ambient atmosphere can hamper pump flow accuracy and accordingly affect drug delivery. If a reservoir is enclosed in a sealed housing, reduction in reservoir volume during emptying can induce a relative negative pressure. Increasing of negative pressure (building of vacuum) may require higher torque and may thus hamper pumping accuracy. Pressure disequilibrium can also happen during altitude changes during flying or mountaineering. Under such circumstances, the relative high pressure within a sealed housing can cause undesirable (i.e., uncontrolled) drug delivery. These effects are likely to occur when the patch unit is fitted with a resilient (collapsible) thin walled reservoir that continuously (or periodically) shrinks during emptying and that may be sensitive to pressure changes.

To improve loudness of an audible notification module (e.g., buzzer) provided within the patch unit. An opening in the patch housing can improve sound delivery from the buzzer contained within a sealed patch unit.

Air may be needed for chemical and electrochemical reactions of one or more of the units/components, such as a battery, located within the patch, that require communication with ambient air, at least partly, to operate. In some embodiments, one or more Zinc-Air batteries may be provided, which may require ingress of air in order to operate properly. A description of such a patch unit is also provided in pending commonly-owned U.S. provisional patent application No. 60/961,484, entitled "Energy Supply Means for Fluid Dispensing Device", and in the non-provisional U.S. non-provisional patent application entitled "Energy Supply for Fluid Dispensing Device", which is being filed on the same date herewith, the contents of both of which are hereby incorporated by reference in their entireties. The Zinc-air batteries are small, lightweight, have high energy capacity, and are relatively inexpensive, thus making them suitable candidates for thin, skin-securable pumps. Zinc-Air batteries typically require ventilation because they chemically react with oxygen from the ambient air to produce electrical energy. Other examples of reactions that may require ingress of air include oxidization of glucose, to measure the amount of glucose in a sample and for in the user body. Oxidization of glucose may be conducted by glucose oxidase as described, for example, in U.S. Pat. Nos. 3,770,607 and 4,679,562, the contents of which are hereby incorporated by reference in their entireties.

In some embodiments of the present disclosure, membranes may be used to provide water tight seal for the housing of a skin-securable (e.g., adherable) patch unit and at the same time to render it permeable to air. The materials from which such membranes may include water repelling fabrics and polymers. Water repelling fabrics may comprise various porous materials (e.g., fabrics), coated with hydrophobic layers that are pervious to air (such materials are also referred to as durable water repellent finishes, water repelling fabrics). Examples of such fabrics are described, for example, in U.S. Pat. Nos. 3,953,566, 4,194,041, 4,560,611 and 4,429,000, the contents of all of which are hereby incorporated by reference in their entireties. Durable water repellent finishes (DWR) are hydrophobic coatings such as polytetrafluoroethylene, perfluoroalkoxy polymer resin and many other types of polymers applied to fabrics to render them water-resistant by causing water to bead up and roll off. Examples of such finishes are described, for example, in U.S. Pat. Nos. 5,688,864, 6,811,884, 6,743,516 and 5,973,055, the contents of all of which are hereby incorporated by reference in their entireties. Polymeric membranes may enable selective passing of certain chemicals (e.g., oxygen) while preventing others chemical or materials (e.g., water) to pass. Generally, nonporous polymeric membranes are used to separate fluids, such as during purification processes in drug and food industries. There, gases and fluids are separated due to their different solubility and diffusivity in polymers. Porous membranes may also be utilized to perform fluid separation. The diameter of the pores of such membranes may be smaller than the mean free path of water molecules. Under standard conditions (e.g., STP conditions of about 1 atm, 300?K), the mean free path of water molecules is approximately 40 nm. Examples of such membranes are described, for example, in U.S. Pat. Nos. 5,352,513, 5,985,475, 7,083,849, 6,676,993, 6,854,603 and 6,638,610, the contents of all of which are hereby incorporated by reference in their entireties.

In some embodiments, a portable programmable fluid dispensing device is provided that is fitted with a water-tight housing that enables not only sealing but also gas transfer.

In some embodiments, one or more water tight housings are provided for a portable programmable fluid dispensing device that enable gas transfer required to cause a chemical reaction.

In some embodiments, a device may be provided that includes a skin-securable dispensing patch unit that is water tight and at the same time pervious to gases. In some embodiments, the device dispenses insulin.

In some embodiments, a miniature portable device for monitoring of glucose is provided that is both water tight and pervious to gases. The continuous monitoring device can be incorporated within an insulin dispensing device, thus endowing it with both sensing and dispensing capabilities. In some embodiments, the device may dispense insulin according to monitored glucose levels within a closed loop system.

In some embodiments of the present disclosure, a simple and inexpensive dispensing patch that is composed of two parts, a disposable part and a reusable part, is provided. After connecting the reusable and disposable parts, the whole device may be water tight and at the same time pervious to gases.

In some embodiments, a dispensing patch unit is provided that delivers fluid into the body. The housing of the device may maintain pressure equilibrium between the device and the ambient atmosphere.

In some embodiments, a device may be provided that delivers fluid into the body. The housing of the device may include at least on opening that enables ingress of air while preventing penetration by water and/or other fluids.

In some embodiments, a device is provided that delivers fluid into the body. At least one housing of the device may include one or more openings that enable ingress of some gases while liquid penetration is prevented.

In one aspect, a fluid dispensing device for delivery of a therapeutic fluid to a user's body is disclosed. The fluid dispensing device includes at least one reservoir to hold the therapeutic fluid, at least one other unit requiring communication with ambient air, at least partly, to operate, and at least one housing defining an interior to retain the at least one reservoir and the at least one other unit, the at least one housing having at least one vent port formed on one or more walls of the at least one housing. The at least one vent port is adapted to direct air into the interior and out of the interior of the at least one housing to maintain pressure equilibrium in the interior of the at least one housing between the air pressure in the interior of the at least one housing and the ambient air pressure outside the at least one housing, and provide communication with ambient air to the at least one other unit requiring air to enable operation of the at least one other unit.

Embodiments of the device may include one or more of the following features.

The at least one other unit requiring communication with the ambient air may include at least one energy source including at least one electrochemical cell to produce electrical energy upon exposure to air. The at least one vent port adapted to direct air may be adapted to direct air into the interior of the at least one housing to provide air to the energy source to enable operation of the at least one energy source.

The at least one energy source may include at least one zinc-air battery.

The at least one vent port adapted to direct air into the interior of the at least one housing to maintain pressure equilibrium in the interior of the at least one housing may be adapted to direct air into the interior of the at least one housing to maintain the pressure equilibrium in the interior of the at least one housing to facilitate controlled delivery of therapeutic fluid from the at least one reservoir retained inside the at least one housing.

The device may further include a semi-permeable membrane covering the at least one vent port, the membrane being impervious to at least one liquid but pervious to at least one gas. The semi-permeable membrane may be impervious to substantially all liquid and may be substantially pervious to air.

The semi-permeable membrane may include a water repelling fabric. The semi-permeable membrane may include a polymer. The semi-permeable membrane may include GORE-TEX™. The semi-permeable membrane may include CELGARD™.

The semi-permeable membrane may provide a rate of gas transfer greater than or equal to about 0.1 micro-liter per hour at a temperature of 300?K and pressure conditions of 1 atm.

The device may further include at least one zinc-air battery and the semi-permeable membrane may provide a rate of gas transfer greater than or equal to about 2.5 micro liter per second at a temperature of 300?K and pressure conditions of 1 atm.

The device may further include an audible notification module disposed in the at least one housing, and the at least one vent port may be further adapted to direct therethrough sound and/or vibration generated by the audible notification module from the interior of the at least one housing to an exterior of the at least one housing to notify the user regarding a condition of the fluid dispensing device.

The at least one housing may include a reusable part including at least a portion of a driving mechanism and electronic components having a processor, and a disposable part having the reservoir, the disposable part being connectable to the reusable part. The at least one vent port may be formed on the disposable part and/or reusable part. The disposable part may be configured to retain at least one energy source comprising at least one electrochemical cell to produce electrical energy, and the reusable part may include the at least one vent port. The disposable part and the reusable part may be substantially sealed.

The disposable part and the reusable part may be substantially sealed when operatively coupled to each other, at least one of the disposable and the reusable part being permeable to ingress of liquids when not operatively coupled to the other part.

The device may further include at least one seal to substantially cover the at least one vent port to prevent entry of air into the at least one housing through the at least one vent port when the device is not in operation.

The at least one other unit may include a sensing element to determine bodily analyte level, the sensing element disposed in the at least one housing. The at least one vent port adapted to direct air may be adapted to provide air to the sensing element to enable operation of the sensing element.

In another aspect, a method is disclosed. The method includes maintaining communication of ambient air with the interior of at least one housing of a fluid dispensing device through a vent port formed on one or more walls of the at least one housing, maintaining pressure equilibrium in the interior of the at least one housing between the air pressure in the interior of the at least one housing and the ambient air pressure outside the at least one housing, and delivering some of the air communicated through the vent port to at least one other unit of the fluid dispensing device that requires communication with the ambient air, at least partly, to operate.

Embodiments of the method may include any of the features described in relation to the device, as well as any one of the following features.

Delivering some of the air to the at least one other unit of the fluid dispensing device may include delivering some of the air to at least one energy source comprising at least one electrochemical cell to produce electrical energy upon exposure of the cell to the delivered air.

Delivering some of the air to the at least one energy source may include delivering the some of the air to at least one zinc-air battery.

Maintaining the pressure equilibrium in the interior of the at least one housing may include maintaining the pressure equilibrium in the interior of the at least one housing to facilitate controlled delivery of therapeutic fluid from at least one reservoir disposed inside the at least one housing, the reservoir adapted to hold therapeutic fluid to be dispensed by the fluid dispensing device.

The method may further include covering the at least one vent port with a semi-permeable membrane, the membrane being impervious to at least one liquid but pervious to at least one gas.

Delivering some of the air to at least one other unit of the fluid dispensing device may include delivering the some of the air to at least one zinc-air battery, and the semi-permeable membrane may provide a rate of gas transfer greater than or equal to about 2.5 micro liter per second at a temperature of 300?K and pressure conditions of 1 atm.

The method may further include directing sound and/or vibrations produced by an audible notification module disposed in the at least one housing from the interior of the at least one housing to an exterior of the at least one housing to notify a user regarding a condition of the fluid dispensing device.

Delivering some of the air to at least one other unit of the fluid dispensing device may include delivering air to a sensor to enable operation of the sensor, the sensor configured to determine bodily analyte level. Delivering air to the sensor to enable operation of the sensor may include delivering air to the sensor to perform glucose oxidization.

BRIEF DESCRIPTION OF THE DRAWINGS

For a better understanding of the devices, systems and methods described herein, including the various objects and advantages thereof, reference is made to the following description, which is to be taken in conjunction with the accompanying illustrative drawings.

DETAILED DESCRIPTION OF THE INVENTION

Disclosed are devices, systems and methods for dispensing fluids, including therapeutic fluids such as, for example, insulin. A fluid dispensing device for delivery of a therapeutic fluid to a user's body includes at least one reservoir to hold the therapeutic fluid, at least one other unit requiring communication with ambient air, at least partly, to operate. Such a device further includes at least one housing defining an interior to retain the at least one reservoir and the at least one other unit. The at least one housing has at least one vent port formed on one or more walls of the at least one housing, that is adapted to direct air into the interior of the at least one housing to maintain pressure equilibrium in the interior of the at least one housing between the air pressure in the interior of the at least one housing and the ambient air pressure outside the at least one housing, and to provide air to the at least one other unit requiring communication with ambient air to enable operation of the at least one other unit. In some embodiments, the at least one other unit includes at least one zinc-air battery that includes at least one electrochemical cell to produce electrical energy upon exposure of the cell to air. Under such circumstances, the vent port adapted to direct air is adapted to direct air to, among other things, provide air to the at least one zinc-air battery to enable operation of the battery.

Figure 1A:
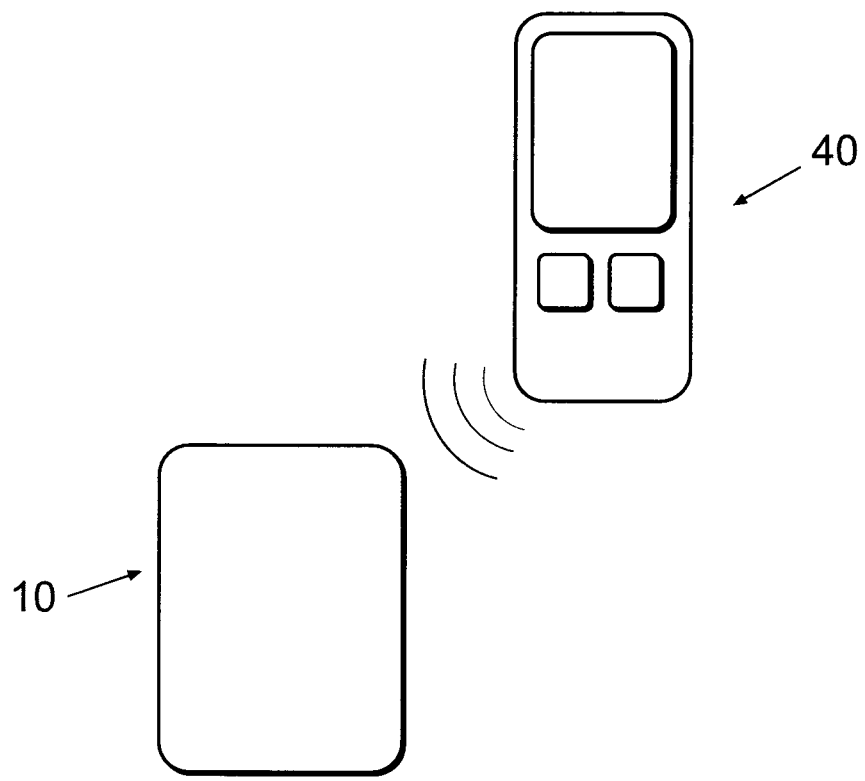
FIGS. 1a-c are schematic diagrams of exemplary single-part and two-part infusion pumps with and without a remote control unit.
Figure 1B:
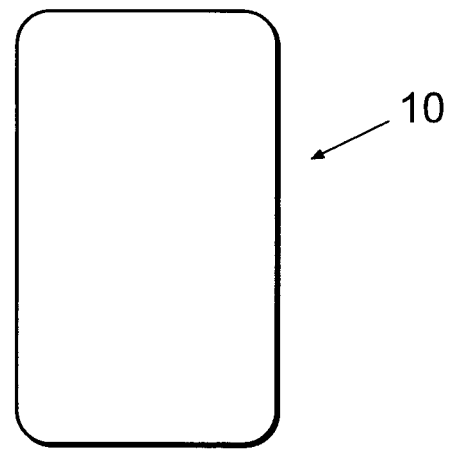
Figure 1C:
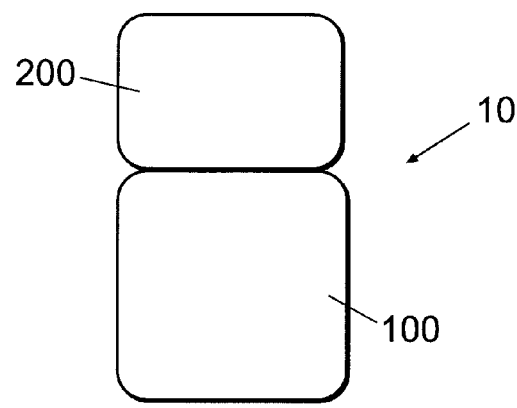

Referring to FIG. 1a, a schematic diagram of a fluid delivery device, also referred to herein as an infusion pump, is shown. The device comprises a dispensing patch unit 10, which can be secured (e.g., adhered to a patient's body), and a remote control unit 40, which communicates with the patch unit 10. The patch unit 10 may be composed of a single part, as shown, for example, in FIG. 1b, or two parts (as shown, for example, in FIG. 1c), namely, a reusable part 100 and a disposable part 200. The patch unit 10 may employ different dispensing mechanisms, such as, for example, a reservoir with a piston, or a peristaltic positive displacement mechanism, e.g., a peristaltic pump with rollers and a stator plate. The dispensing patch unit may include a user interface that includes buttons (not shown) to enable manual fluid delivery programming.

Figure 2A:
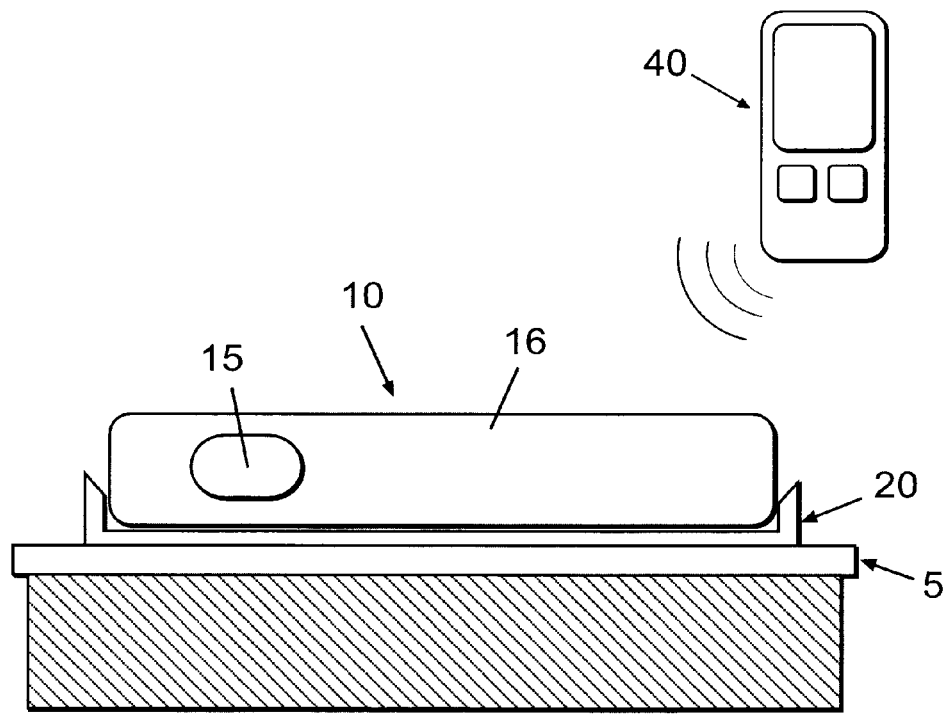
FIGS. 2a-b are schematic diagrams of exemplary single part and two-part dispensing patch units, respectively, secured to a patient's skin using a cradle.

Referring to FIG. 2a, a fluid delivery device comprising a single-part dispensing patch unit 10 having a housing 16, a cradle unit 20 and a remote control unit 40 is shown. The patch unit 10 is connectable to cradle unit 20 securable (e.g., through adhesion) to the patient's skin 5. The patch unit 10 may be disconnected from or reconnected to the cradle unit 20 at the patient's discretion. A needle unit that may include a cannula and a penetrating member (not shown) may be inserted through the cradle unit into the patient's body. Fluid delivery can be controlled through programmed profiles and instructions, programmed, for example, by the remote control unit 40, or provided manually through at least one button 15 provided on the patch unit 10 (e.g., disposed on the housing 16 of the patch unit).

Figure 2B:
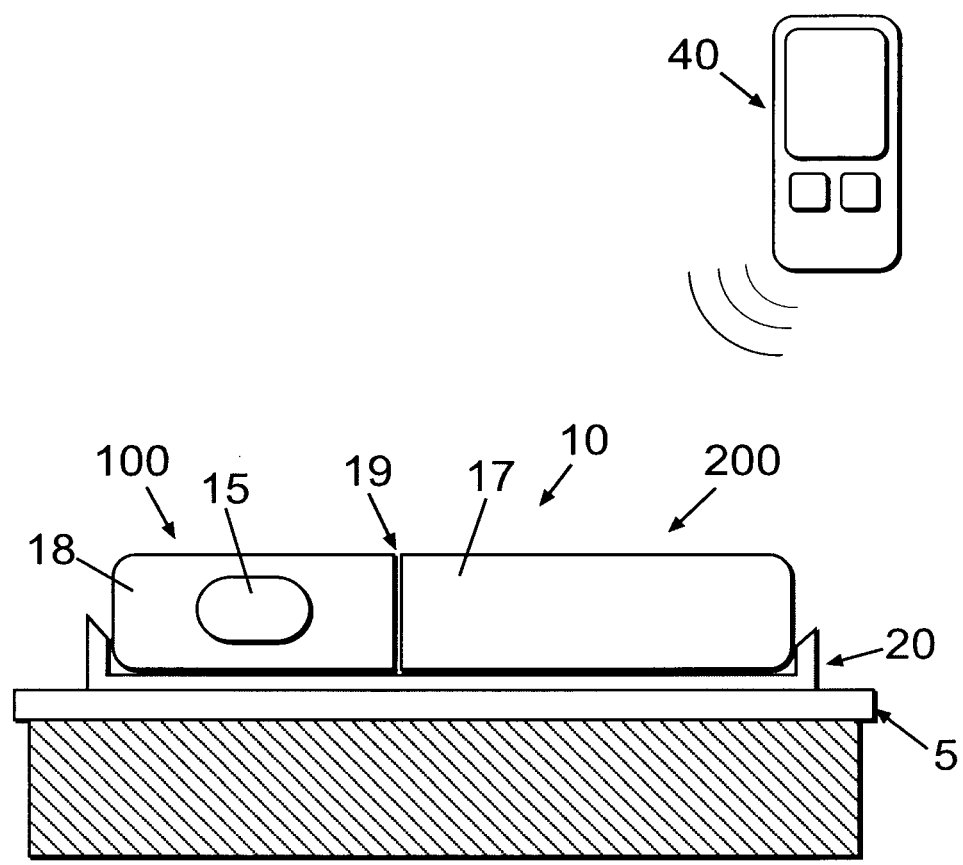

Referring to FIG. 2b, a fluid delivery device comprising a two-part dispensing unit 10 that includes a reusable part 100 and its housing 18, a disposable part 200 and its housing 17, a cradle unit 20 and a remote control unit 40 is shown. One or more manual buttons 15, constituting a user-interface, may be located on the reusable part 100 of the patch unit 10. The reusable part 100 and the disposable part 200 are connectable at the interface 19.

The depicted configurations of fluid delivery devices, such as those shown in FIGS. 2a-b, which comprise a patch unit, a cradle unit and a needle unit as detailed herein are also described in commonly-owned patent applications Israeli Patent Application No. IL 171813, U.S. Publication No. 2007/0106218 (corresponding to U.S. patent application Ser. No. 11/397,115, entitled "Systems and methods for sustained medical infusion and devices related thereto"), U.S. application Ser. No. 11/706,606, filed Feb. 14, 2007, and U.S. provisional application Nos. 60/833,110, filed Jul. 24, 2006, 60/842,869, filed Sep. 6, 2006, and 60/848,511, filed Sep. 29, 2006, the contents of all of which are hereby incorporated by reference in their entireties. One of the advantages of the two-part configuration, shown, for example, in FIG. 2b, is that the relatively expensive units/components of the fluid delivery device may be deployed within the reusable part, while the less expensive unit components of the device may be accommodated within the disposable part.

Figure 3A:
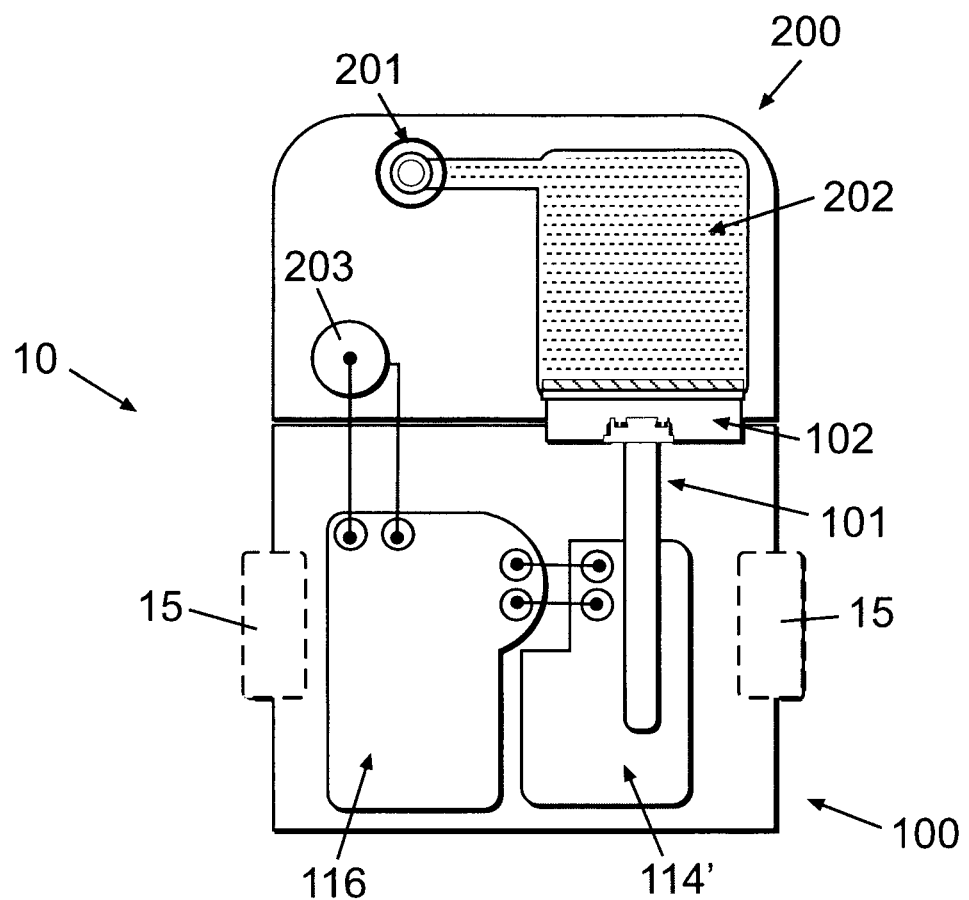
FIGS. 3a-b are schematic diagrams illustrating operation of an exemplary two part dispensing patch unit which includes a piston-type displacement pumping mechanism that comprises a propelling plunger.
Figure 3B:
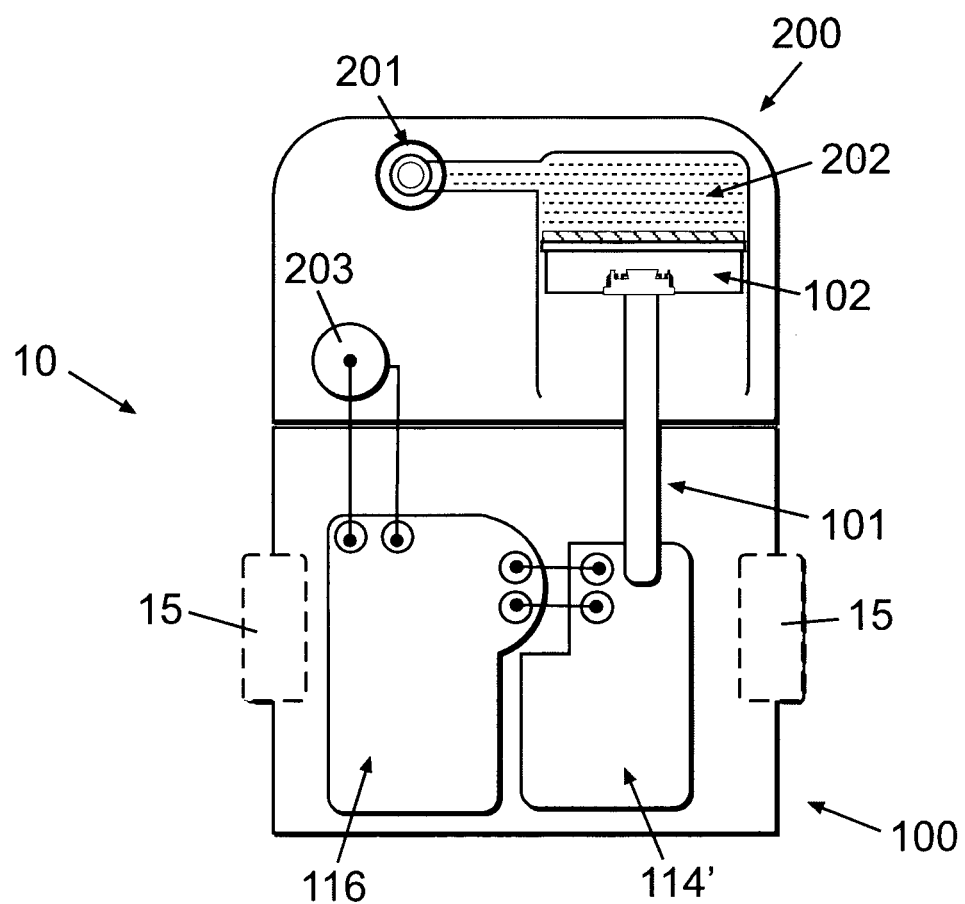

Referring to FIGS. 3a and 3b, schematic diagrams of an exemplary dispensing patch unit 10 in operation are shown. The depicted dispensing patch unit 10 is implemented using an infusion pump which includes a piston-type displacement pumping mechanism that comprises a propelling plunger and is configured to deliver fluid through interaction of a piston with the fluid reservoir retained in the housing of the disposable part 200. Such a configuration is also disclosed in commonly-owned U.S. provisional application No. 60/928,815, entitled "A positive displacement pump", filed May 11, 2007, the content of which is hereby incorporated by reference in its entirety. As noted, in some embodiments, the patch unit may include two parts, namely, the reusable part 100 and the disposable part 200.

The disposable part 200 may comprise:
An outlet port 201 for delivering the therapeutic fluid to a patient's body.
A reservoir 202 that stores the therapeutic fluid (e.g., insulin).
A power source 203 that includes one or more energy sources, such as batteries, to energize the electrical units/components of the infusion pump.
A threaded rod 101 and plunger 102 that are components of the dispensing mechanism.

The reusable part 100 may comprise:
One or more manual buttons 15, forming at least part of a user-interface disposed on the patch unit, to adjust the amount of therapeutic fluid to be delivered, particularly for a bolus dosage.
A displacement driving mechanism 114', including a motor and a gear. This part of the driving mechanism moves a piston, which, in some embodiments comprises the threaded rod 101 and the plunger 102 that, as noted, may be included in the disposable part 200.
Electronic components 116 such as controller, processor and transceiver.

As shown in FIG. 3a, the piston infusion pump 10 includes a full fluid reservoir 202. The threaded rod 101 and the plunger 102 are pulled back so that the plunger 102 is positioned proximate to the interface where the disposable part 200 and the reusable part 100 connect to thus provide maximal volume for the therapeutic fluid in the reservoir 202. FIG. 3b shows the piston infusion pump after delivery of therapeutic fluid, as a result of which the fluid reservoir is emptied. Particularly, to deliver the therapeutic fluid, the threaded rod 101 and the plunger 102 are moved to cause the therapeutic fluid to be pushed out of the reservoir 202 to the patient's body through the outlet port 201. The change in position of the plunger 102 thus reduces the volume of the reservoir 202.

Figure 4A:
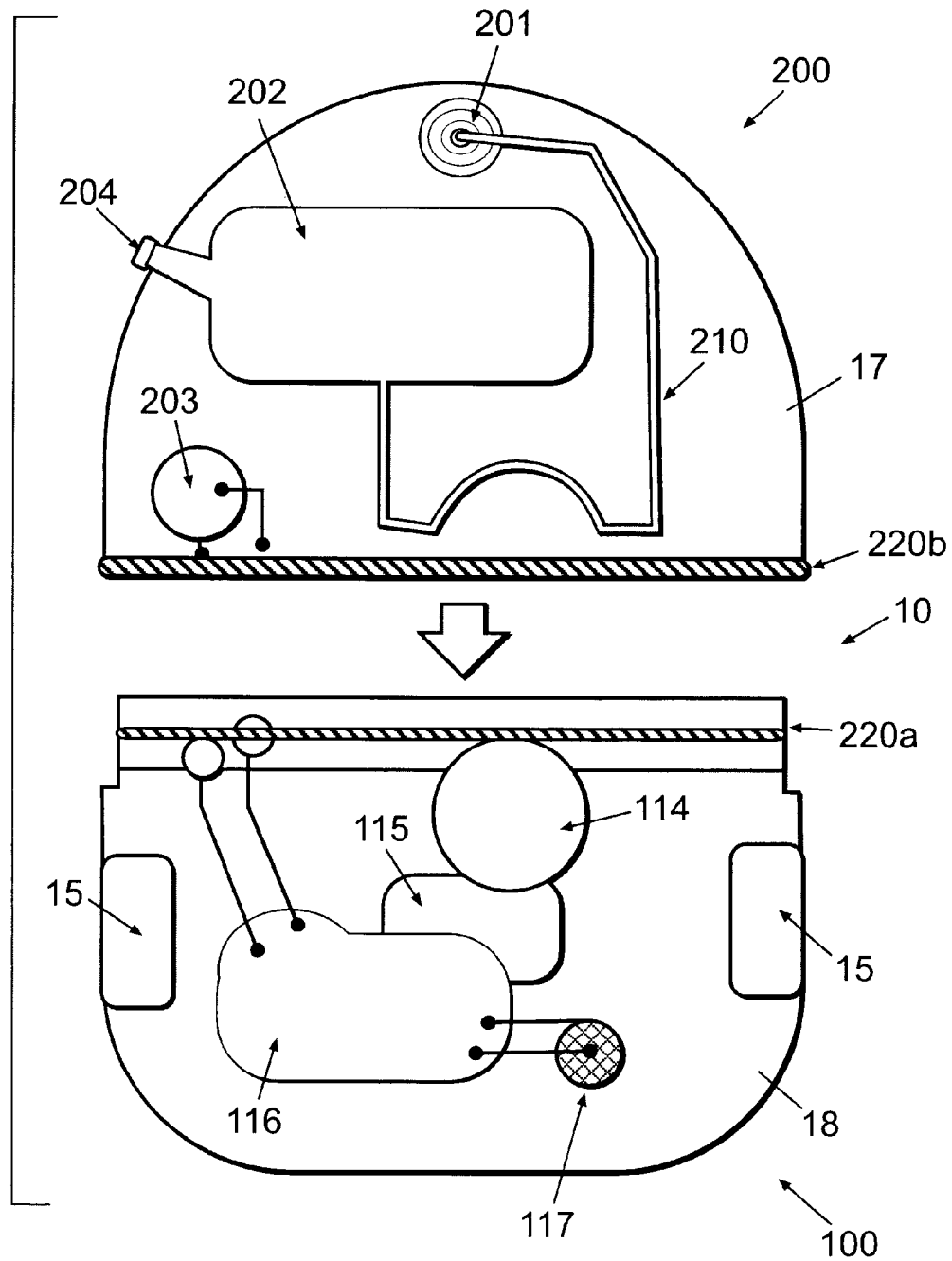
FIGS. 4a-b are schematic diagrams of an exemplary sealable two part dispensing patch unit.
Figure 4B:
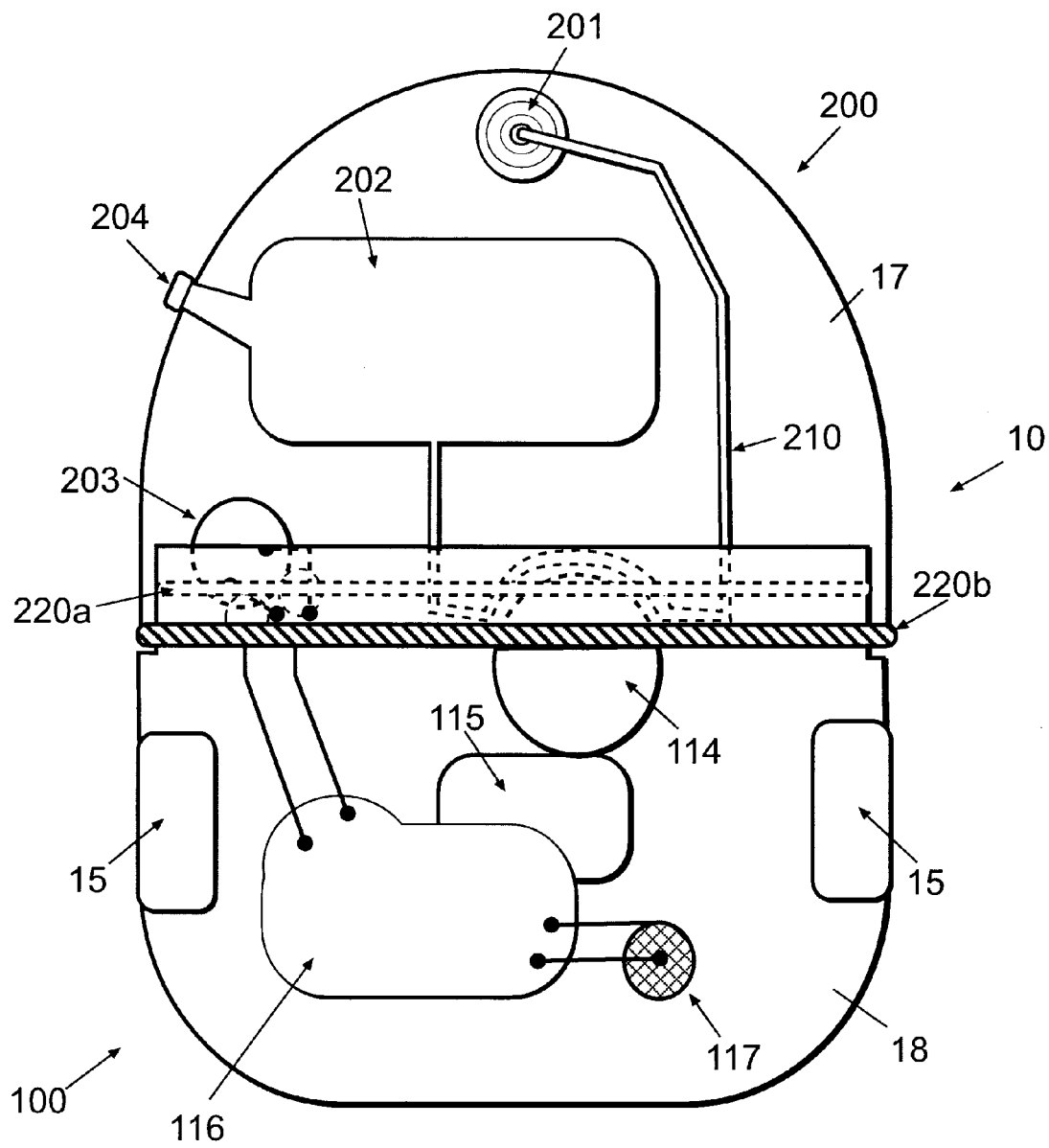

Referring to FIGS. 4a and 4b, schematic diagrams of another exemplary dispensing patch are shown. Particularly, a sealable dispensing patch unit 10 comprises two parts, namely, a reusable part 100 and a disposable part 200 that are similar to those described, for example, in commonly-owned U.S. provisional application No. 60/922,794, entitled "Apparatus and method for pumping fluid into a mammal's body", filed Apr. 10, 2007, the content of which is hereby incorporated by reference in its entirety. The disposable part 200 includes a gasket 220b. Another gasket 220a is coupled to the reusable part 100. These gaskets are, in some embodiments, flat gasket, o-ring types, or other types of seals that may be applied. The gasket 220a may be coupled to the housing 18 of the reusable part 100 by welding, gluing, or other coupling mechanism or procedure, and/or may be positioned in a trench in the housing 18. The gasket 220b may be coupled to the housing 17 of the disposable part 200. Thus, the gaskets remain in their places even when the parts 100 and 200 of the dispensing patch unit are separated, as shown in FIG. 4a. The gasket configurations may include at least one o-ring, and/or other gasket(s) that may be provided with the reusable part or the disposable part.

FIG. 4b shows the disposable part 200 connected to the reusable 100 part. The gaskets 220a and 220b maintain sealing (as also shown in FIGS. 5a-d) of the dispensing patch unit 10 after attaching the reusable part 100 to the disposable part 200. The sealing may be achieved by the application of pressure on the gaskets as shown, for example in FIGS. 5a-d.

The disposable part 200 depicted in FIGS. 4a and 4b may include:
An outlet port 201.
A reservoir 202.
At least one energy source such as a battery 203.
A filling port 204.
A delivery tube 210.

The reusable part 100 of FIGS. 4a and 4b may include:
A user interface that may include one or more buttons 15 for manual fluid delivery programming.
A driving mechanism 115 to actuate the pumping mechanism.
A peristaltic-based pumping mechanism rotary wheel 114.
A controller implemented, for example, using an electronic control system arranged on a printed circuit board (PCB) 116.
An audible notification module that may include a buzzer 117 to provide alarms to alert a user (e.g., the patient) regarding certain conditions of the dispensing device.

When the disposable part 200 is coupled to the reusable part 100, the rotary wheel 114 actuates the delivery tube to compress a section of the delivery tube to thus cause displacement of the therapeutic fluid towards the outlet port 201 of the disposable part 200.

Figure 5A:
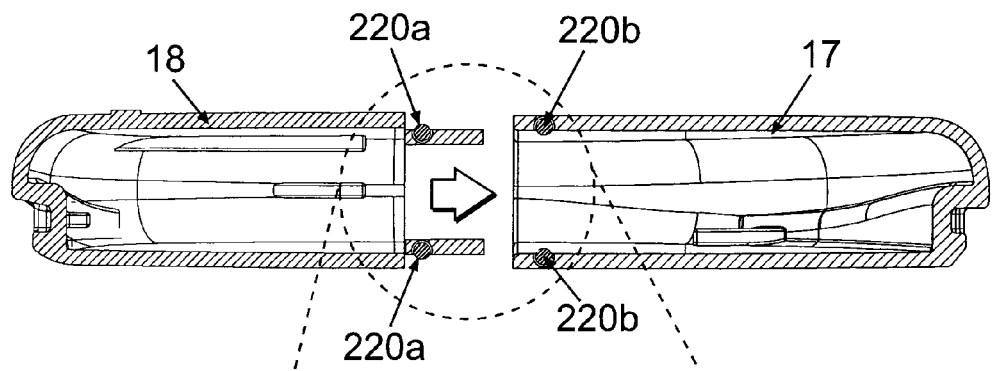
FIGS. 5a-d are schematic diagrams of exemplary embodiment of a sealed fluid dispensing device.
Figure 5B:
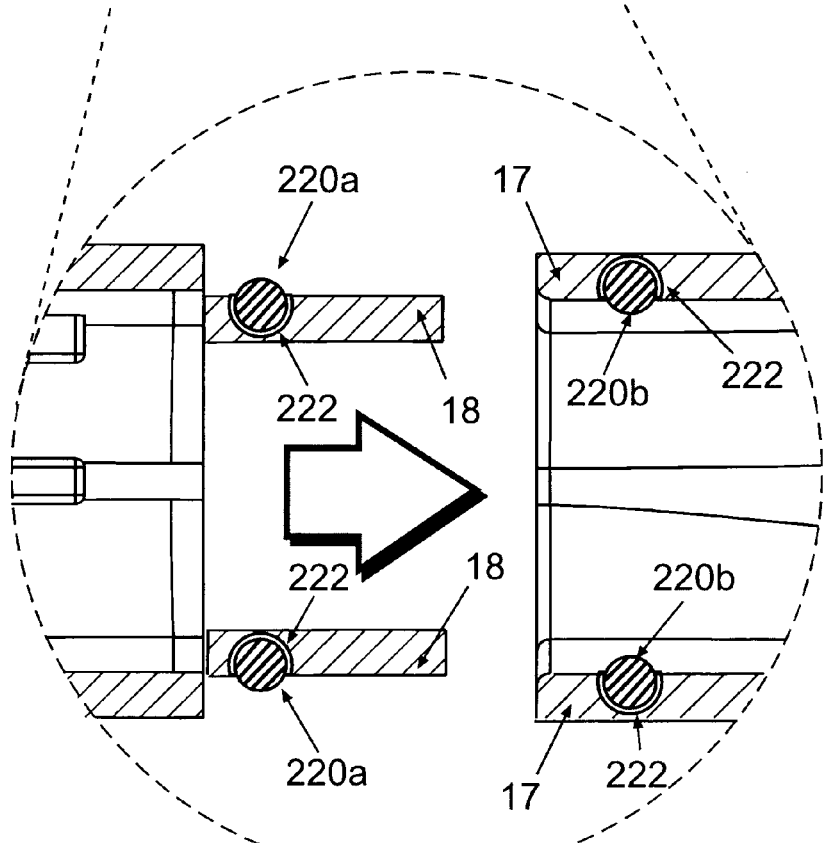
Figure 5C:
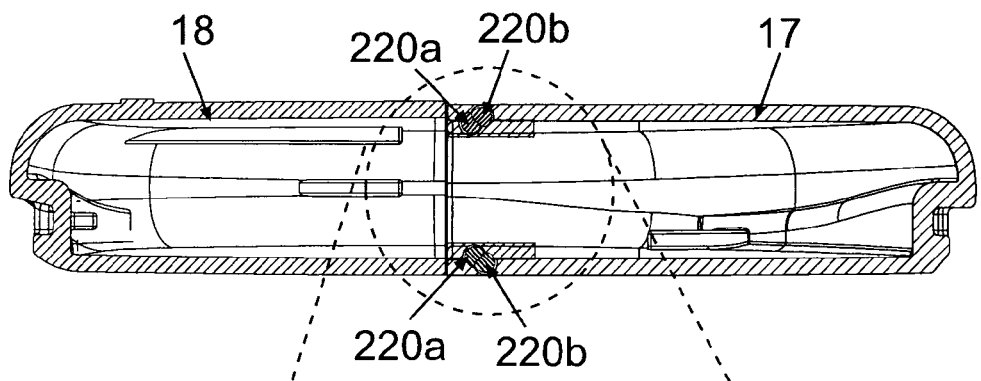
Figure 5D:
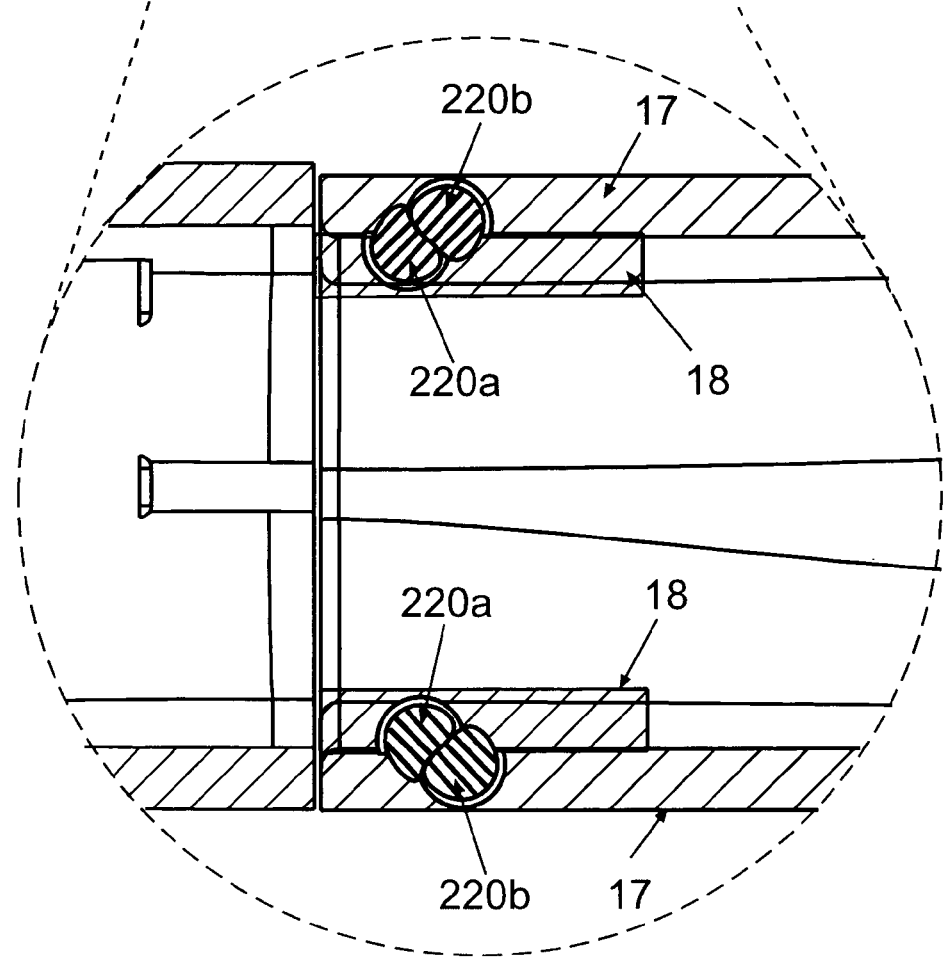

Referring to FIGS. 5a-d, cross-sectional diagrams of a dispensing patch unit with sealing are shown. Particularly, in these figures, the interface between the housing 18 of the reusable part 100 and the housing 17 of the disposable part 100 are shown. FIG. 5a shows the separated disposable and reusable parts, aligned and facing each other ready for attachment (FIG. 5b is an enlarged view of part of the view shown in FIG. 5a). FIG. 5c depicts the disposable part attached to the reusable part (FIG. 5d is an enlarged view of part of the view shown in FIG. 5c). As shown, the gaskets 220a and 220b are received in trenches 222 defined in the housings of the disposable and/or the reusable parts to facilitate maintaining the gaskets in place.

Figure 6A:
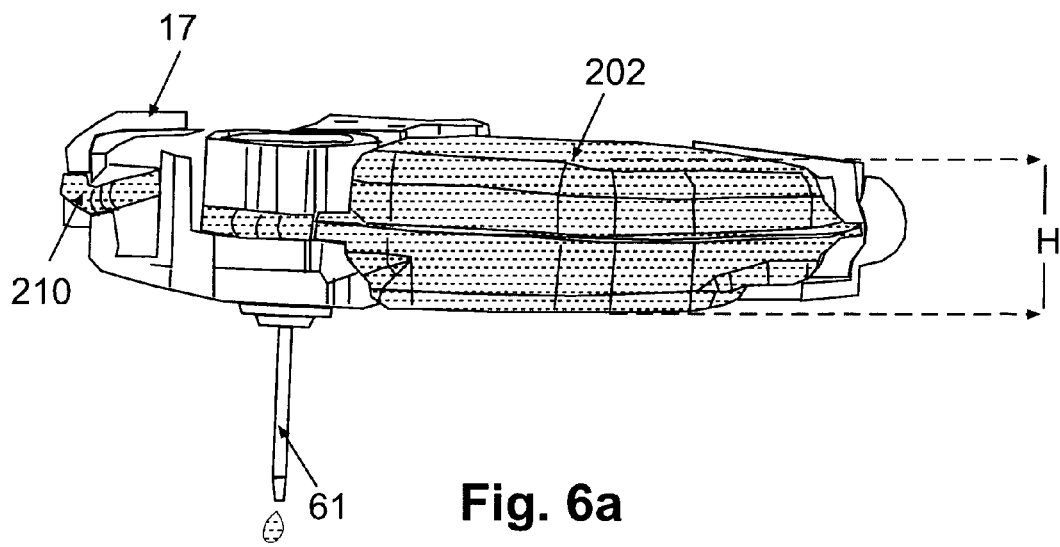
FIGS. 6a-b are schematic diagrams illustrating operation of an exemplary fluid dispensing device that includes a collapsible reservoir.
Figure 6B:
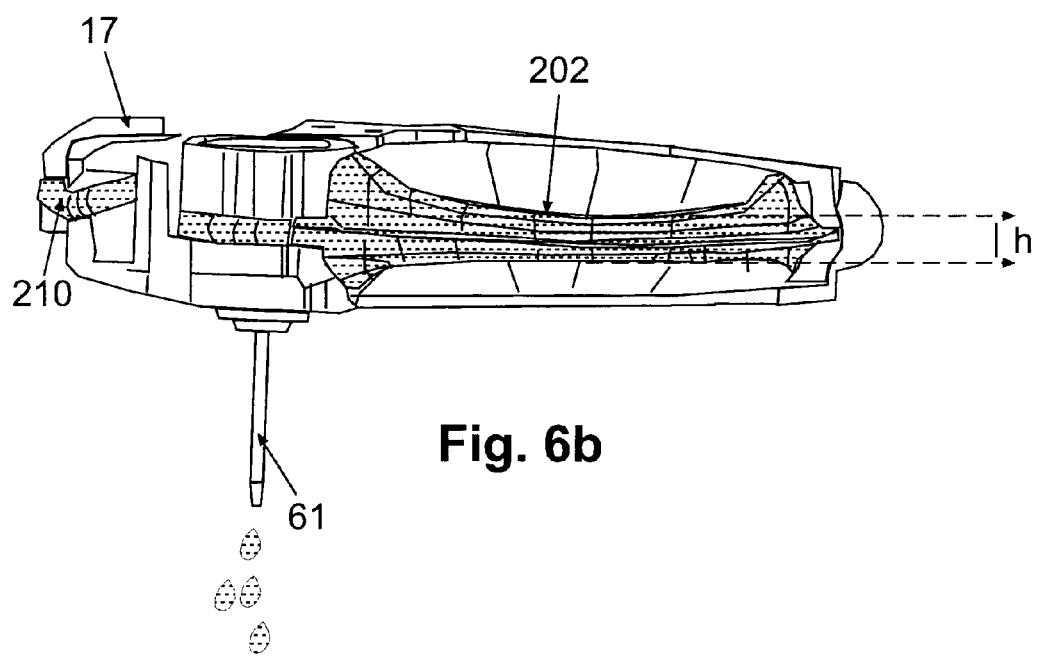

Referring to FIGS. 6a and 6b, schematic diagrams of an exemplary dispensing device having a collapsible reservoir 202 is shown. Further descriptions of similar collapsible reservoirs are provided, for example, in co-pending and co-owned U.S. provisional application No. 60/961,528, entitled "Collapsible Pump Reservoir", filed Jul. 20, 2007, and co-owned U.S. non-provisional patent application entitled "Collapsible Reservoir for Use with a Delivery Device" which is being file on the same date as the instant application, the contents of both of which are hereby incorporated by reference in their entireties. A collapsible reservoir is suitable for use with peristaltic pumps. The fluid within the reservoir 202 is displaced by the forcibly induced peristaltic movement along the delivery tube 210. The reservoir 202 is configured to collapse while emptying, to compensate for the displaced fluid and to avoid entry of air. In some embodiments, the collapsible reservoir is positioned in the housing 17 of the disposable part. FIG. 6a shows a full collapsible reservoir 202 while FIG. 6b shows the reservoir after some of the fluid that was held in it had been removed (e.g., delivered to the patient). As shown, the volume of the collapsible reservoir 202 is decreased when the reservoir is being emptied, e.g., the dimensions, such as the height of the full reservoir "H" (as indicated in FIG. 6a), are larger than the dimensions, such as the height "h" of the depleted reservoir (as indicated in FIG. 6b). The depicted dispensing system also includes a cannula 61 for the delivery of the therapeutic fluid from the dispensing patch to the patient's body. The cannula is inserted into the patient body and is in fluid communication with the delivery tube 210 (as shown in FIGS. 6a and 6b).

Figure 7:
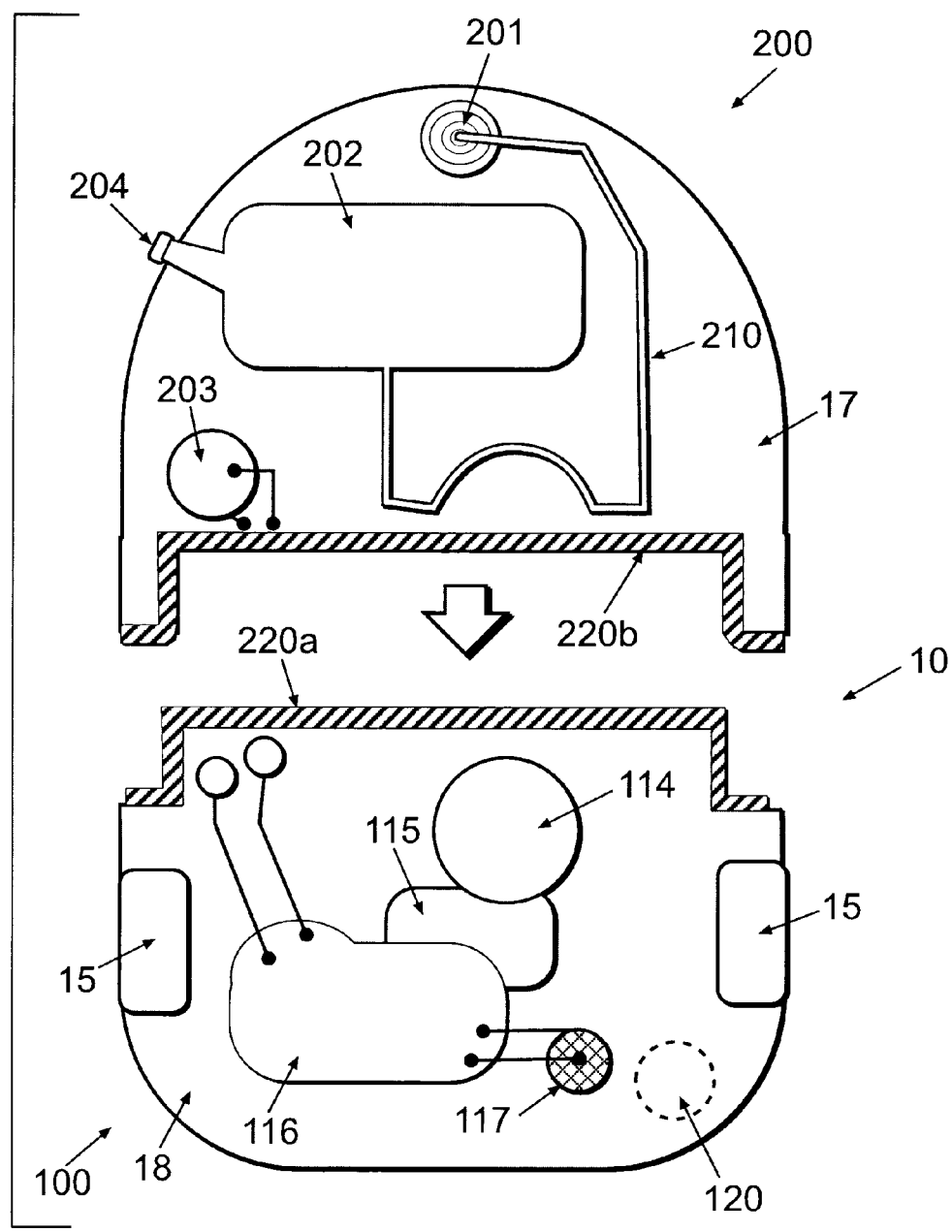
FIG. 7 is a schematic diagram of an exemplary sealable two part dispensing patch unit provided with a vent.

Referring to FIG. 7, a schematic diagram of an exemplary sealable dispensing patch unit 10 is shown. The dispensing patch comprises two parts, namely, a reusable part 100 and a disposable part 200. A face seal is employed to seal the dispensing patch 10 unit. Particularly, sealing may be achieved by using a first gasket (or o-ring, or any other sealing device) 220a coupled to the reusable part 100, and a second gasket 220b coupled to the disposable part 200. The gaskets may be prepared using pre-made molds corresponding to the shapes of the contours of the respective houses to which the gaskets (or other sealing devices) are to be coupled to. As described in greater details below, an example of a face seal is provided in FIGS. 8a and 8b. Returning to FIG. 7, the dispensing device includes a vent aperture (also referred to as a vent, or a vent port) 120 formed on one or more of the walls of the housing(s) of the dispensing device to enable gas (e.g., oxygen) to enter and exit the sealed patch unit after the disposable and reusable parts are attached. In the exemplary dispensing patch unit (device) depicted in FIG. 7, the vent port is formed in one or more of the walls of the housing 18 of the reusable part 100. Vent(s) similar to the vent 120 may be provided in the housing(s) of any other of the embodiments of the dispensing devices disclosed herein.

In some embodiments, air passage to direct air into the interior defined by at least one housing of the dispensing device may be required to, among other things, balance the pressure between the interior of the at least one housing (which may be watertight or sealed) and the ambient air. Pressure differences between the interior defined by the at least one housing of the dispensing patch unit may result due to altitude changes and/or to changes in the volume of the therapeutic fluid or the reservoir containing the fluid. Air communication with the interior defined by the at least one housing of the dispensing patch unit (dispensing device) may also be required to enable operation of at least one unit/component of the dispensing device that requires communication with ambient air, at least partly, to operate (an example of such a unit/component includes a zinc-air battery that requires air to operate). In some embodiments, the vent 120 may be covered by a selective membrane to prevent water entrance to the dispensing patch unit, thus making the unit water tight. In some embodiments, the vent may be positioned in the vicinity of the of an audible notification module, such as a buzzer 117, to provide increased loudness of sounds or vibrations produced by the buzzer 117. The at least one vent port formed in the wall(s) of the at least one housing is thus further adapted to deliver or transmit the sound waves and/or vibrations produced by the buzzer to the exterior of the at least one housing of the dispensing device. The vent port(s) may be positioned, in some embodiments, in other locations of the at least one housing of the dispensing patch unit.

The disposable part 200 of the dispensing patch unit depicted in FIG. 7 may also include:
An outlet port 201.
A reservoir 202.
At least one energy source such as a battery 203.
A filling port 204.
A delivery tube 210.

The reusable part 100 of the dispensing patch unit depicted in FIG. 7 may comprise:
A user-interface that includes, for example, one or more buttons 15 to enable, for example, manual fluid delivery programming.
A driving mechanism 115.
A peristaltic mechanism rotary wheel 114.
A controller implemented, for example, using an electronic control system arranged on a printed circuit board (PCB) 116.

The dispensing patch unit 10 may also include a sensing unit, to measure, for example, a glucose level in the patient's body to thus implement a closed loop fluid delivery system.

Figure 8A:
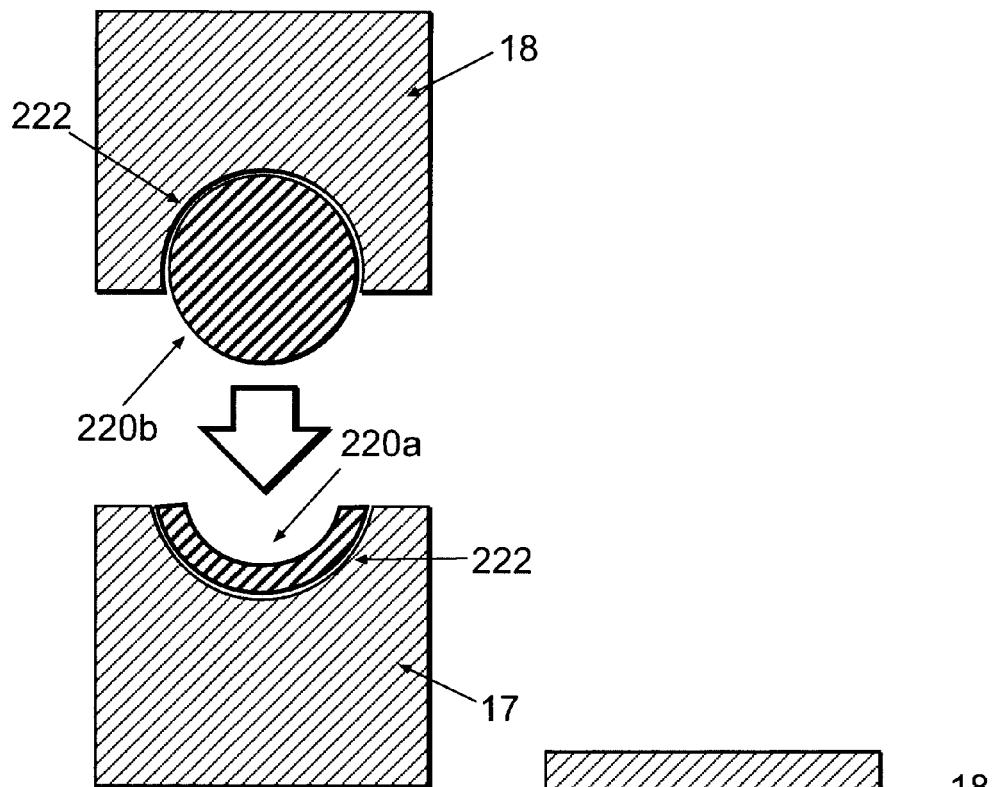
FIGS. 8a-b are cross-sectional diagrams of an exemplary sealed fluid dispensing device.
Figure 8B:
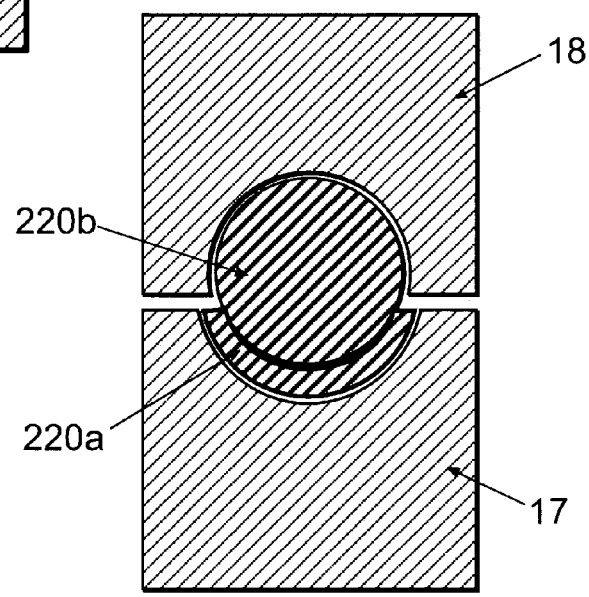

With further reference to FIGS. 8a and 8b, cross-sectional diagrams of an exemplary face seal are shown. Two gaskets (or o-rings) 220a and 220b, received in trenches 222, have complementary cross-sectional shapes so that one gasket (or some other type of seal) fits within the other to maintain proper sealing. In some embodiments, the gasket with a "C" shaped cross-section is coupled to the housing 17 of the disposable part while the gasket having the "O"-shaped cross-section is coupled to the housing 18 of the reusable part. FIG. 8b shows the two gaskets brought in close proximity to each other to reliably seal the dispensing patch unit after attaching the reusable and the disposable part.

Figure 9A:
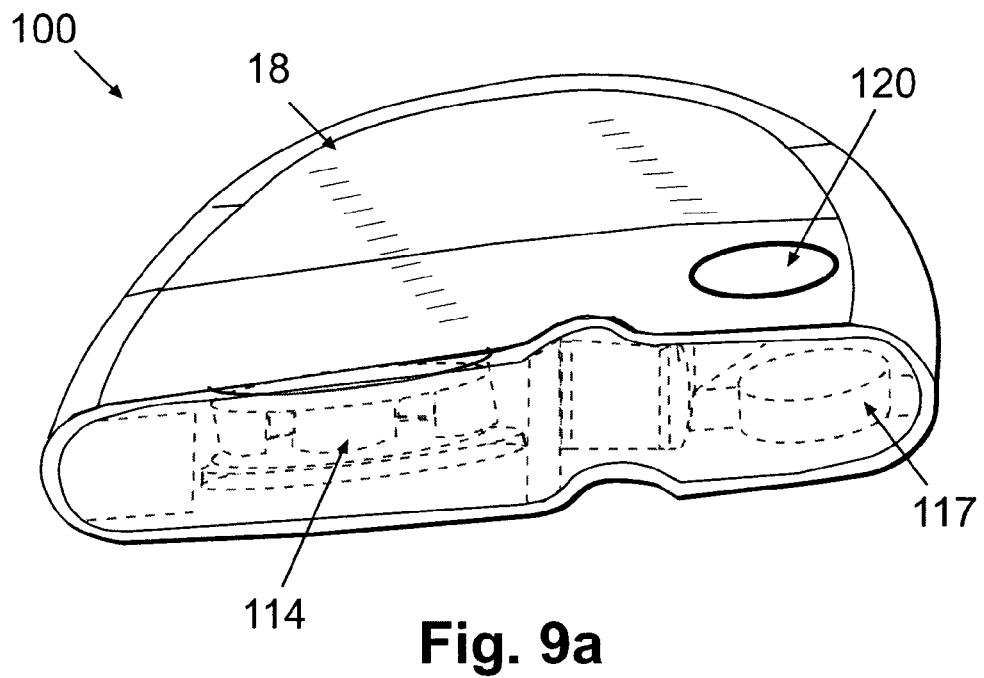
FIGS. 9a-b are perspective views of an exemplary reusable part of the dispensing patch having a vent with and without, respectively, a selectively permeable membrane.
Figure 9B:
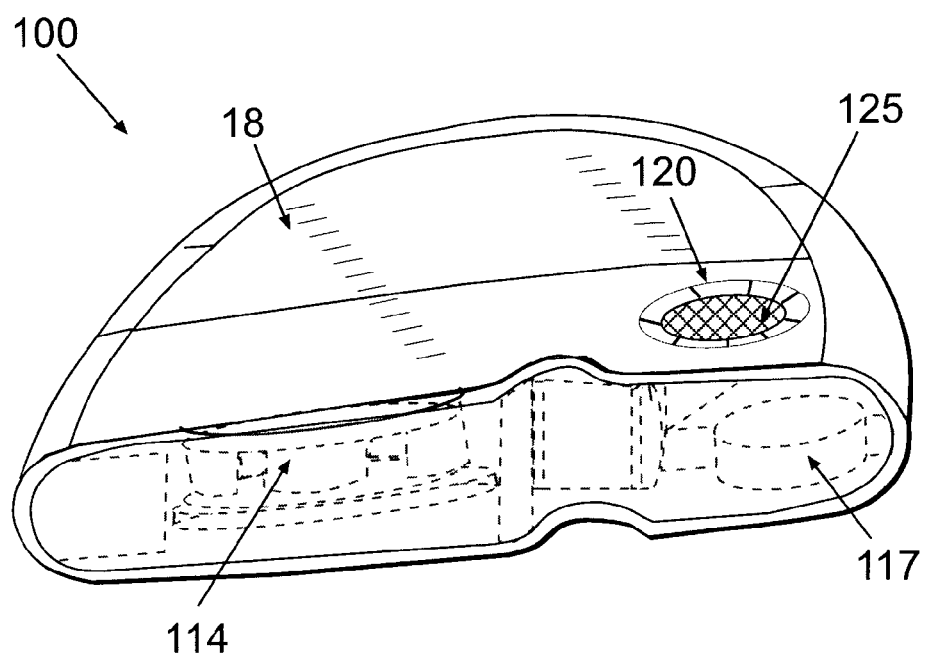

Referring to FIGS. 9a and 9b, perspective views of an exemplary reusable part 100 that includes a vent port 120 are shown. The vent port may be covered, in some embodiments, with a selectively permeable membrane 125 (as shown in FIG. 9b). In some embodiments, the open surface area of the membrane 125 may be large enough to enable minimal flow of 0.1 µl/hour of gas across it under standard conditions (STP). A flow of 0.1 µl/hour of gas, which is derived from the minimal basal flow of insulin dosage for a child, is required to enable pressure equilibrium between the interior of the housing and the ambient air. Generally, when the volume occupied by the fluid is reduced, the empty volume in the housing is increased, thus reducing the internal pressure in the housing. Pressure differential (i.e. when pressure equilibrium between the interior of the housing to the ambient air is disrupted) may cause inaccurate fluid delivery, increased power consumption and the like.

In some embodiments, the vent 120 is positioned proximate to the buzzer 117, which is one of the components of the reusable part 100. This physical configuration of the reusable part facilitates transmission of sound/vibrations produced by the buzzer to the outside of the device, thus improving the alarm performance of the device.

Figure 10:
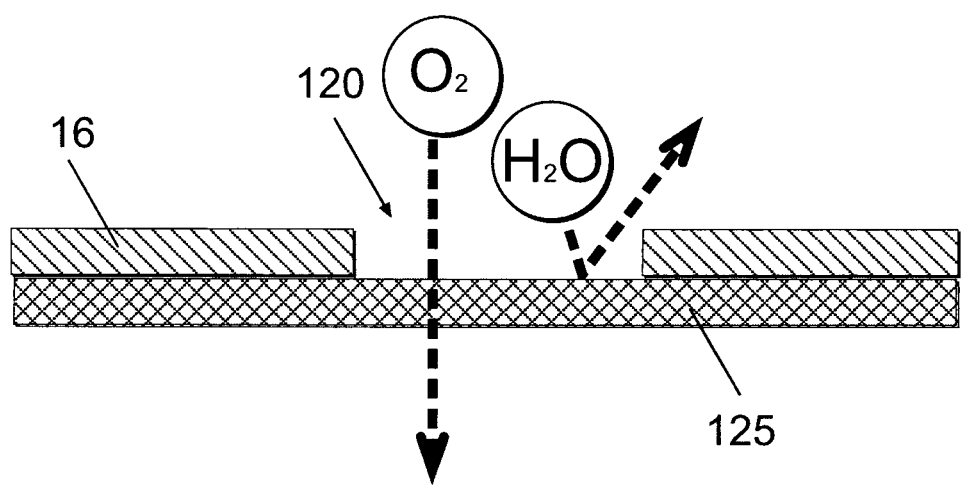
FIG. 10 is a partial schematic diagram of an exemplary dispensing patch's housing closed by a selectively permeable membrane.

Referring to FIG. 10, a partial cross-sectional diagram of an exemplary selectively permeable membrane 125 is shown. In some embodiments, the membrane 125 covers the vent 120 formed on one or more of the walls of the at least one housing 16 of a dispensing patch unit. In the illustrated embodiment, the vent 120 may be provided in the housing proximate to an audible notification module (e.g., a buzzer) to improve the alarm performance of the device In some embodiments, the vent 120 may be provided proximate to an air-operated battery (e.g., a zinc-air battery) and/or a glucose oxidase sensor to provide air (oxygen) to enable operation of one or more of those units. In some embodiments, the vent 120 may be positioned close to the reservoir holding the therapeutic fluid to facilitate the pressure balancing functionality of the dispensing device. In some embodiments, a two-part dispensing patch unit may include a vent 120 that may be provided in the housing of the disposable part, in the housing of the reusable part, or in both of them. There may be more than one vent in the housing of the dispensing patch unit.

The membrane 125 covering the at least one vent port may be formed from any suitable material such as, for example, a GORE-TEX™ fabric. The selectively permeable membrane is, in some embodiments, water tight and at the same time pervious to at least one gas (e.g., oxygen). In some embodiments, the membrane may enable minimal air flow of 0.1 μl per hour to enable delivery of the minimal dosage of insulin for a child. In some embodiments, materials that enable other air flows rates may be used. For example materials that enable an air flow of about 1 ml per minute may be used in circumstances where the dispensing patch unit is used during flight. In some embodiments, when applying a membrane 125 with air permeability of 5 liter per sec of 1 square meter of the membrane, the available area of the membrane for air flow may be at least 0.03 mm$^2$ to enable pressure balancing during flight. Other requirements that may affect the attributes of the membrane 125 include the type of the battery used in conjunction with the dispensing patch unit. For example, zinc air button batteries may require about 0.5 mm$^2$ of membrane surface area to enable oxygen flow rate of 2.5 micro liters per second. It should be noted that the surface area of the membrane available for gas transfer is described herein only as an example, and that many other parameters may affect the size of the membrane, including the membrane's permeability, manufacturing and assembly processes, minimal gas flow capability, etc. The vent 120 may take any suitable form such as, for example, having contour(s) that are polygonal, circular, elliptical, amorphous and the like.

The membrane may be pervious to other gases, including nitrogen, carbon dioxide ($CO_2$), etc., and it may be impervious to some other gases such as, for example, hydrogen sulfide, water vapors and NOXs (nitrogen oxides). The selectively permeable membrane should be impervious to aqueous solutions such as sea water, beverages (e.g., soda and juices) and food (e.g., soup and porridge). The selectively permeable membrane may also be impervious to other fluids that may damage the dispensing patch, including alcohol and cooking oil.

Figure 11A:
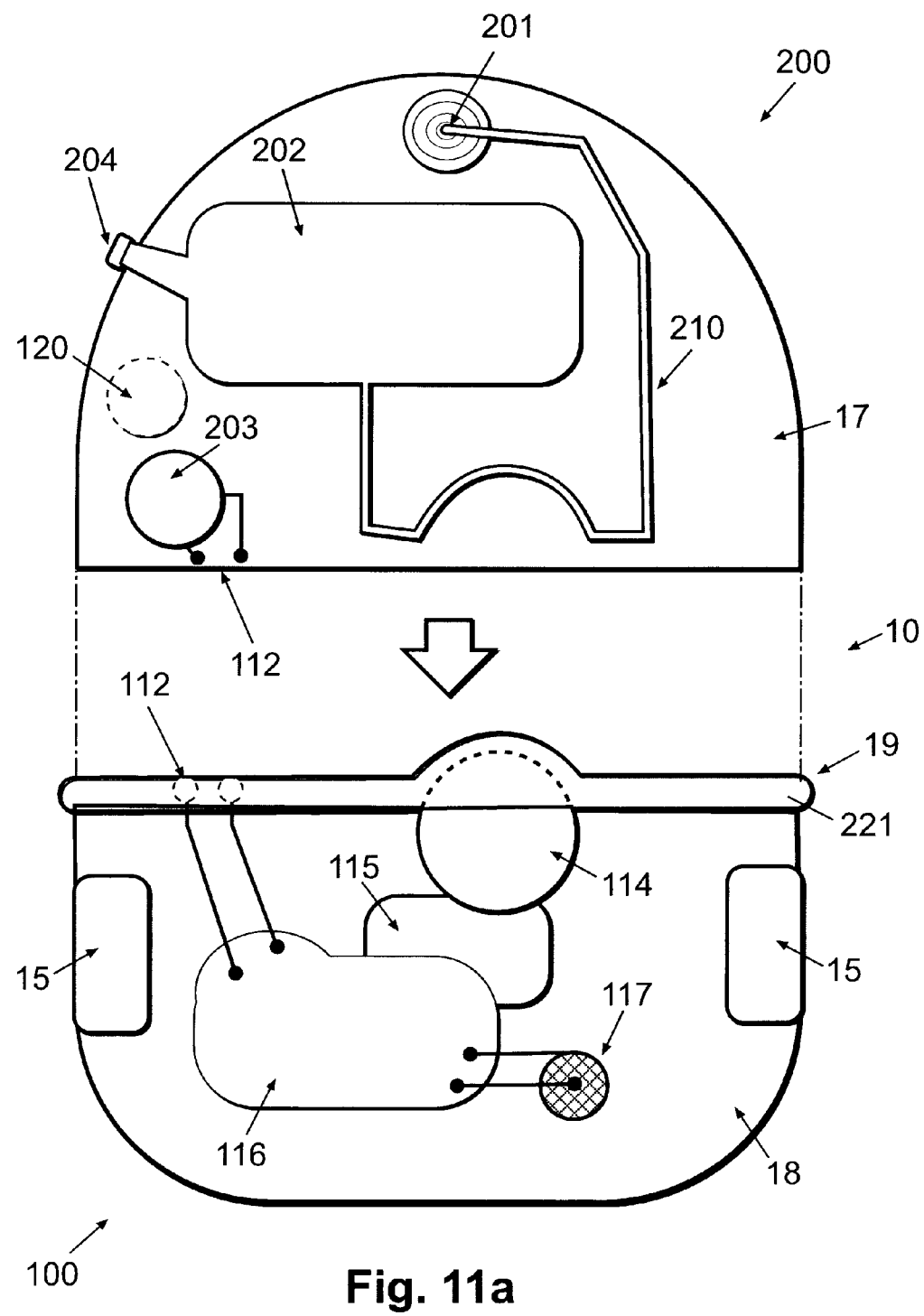
FIGS. 11a-b are schematic diagrams of an exemplary two-part dispensing patch unit comprising a sealed reusable part and a sealed disposable part.
Figure 11B:
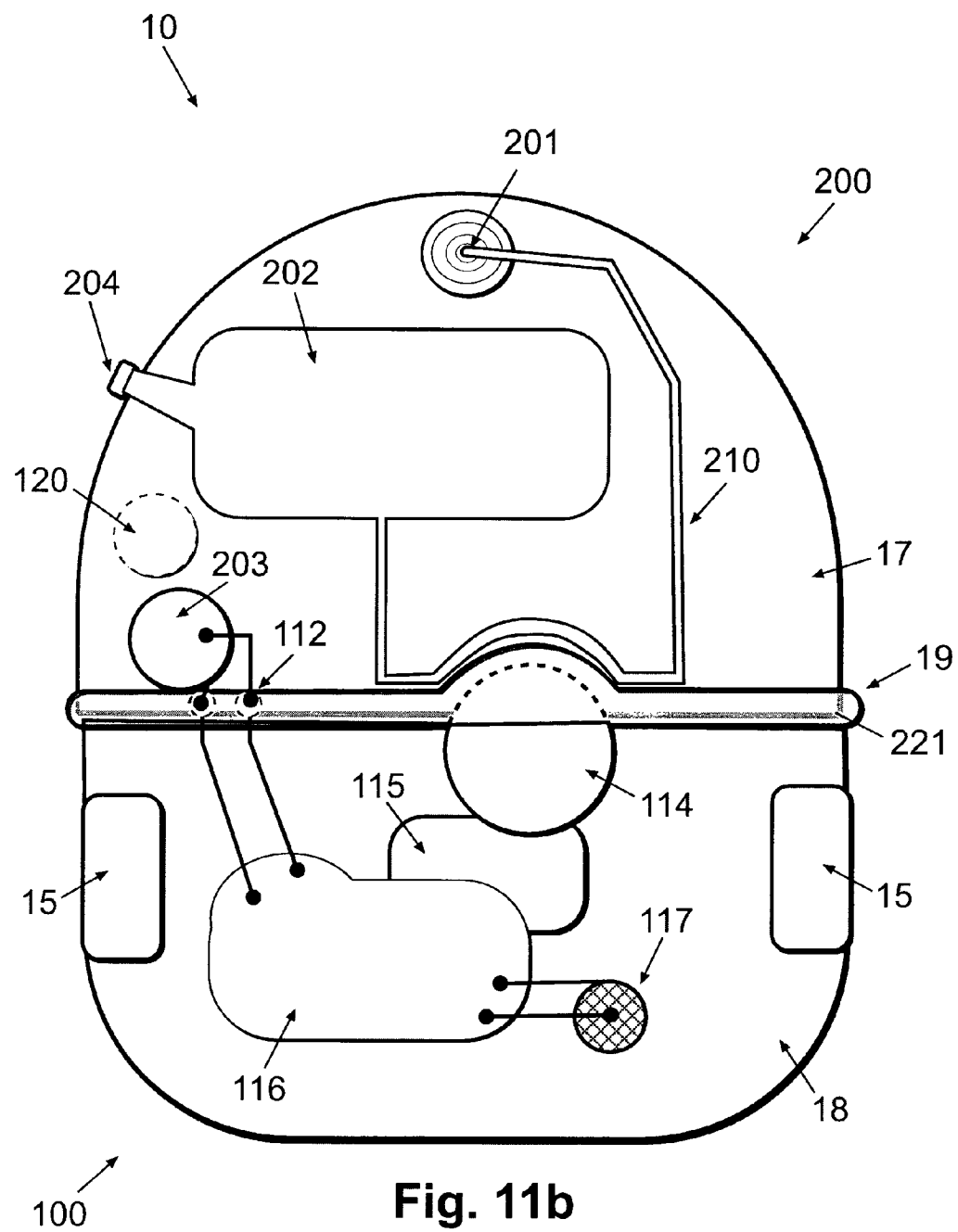

Referring to FIGS. 11a and 11b, schematic diagrams of an exemplary two-part dispensing patch unit with a sealed reusable part 100 and a sealed disposable part 200 are shown. Each of the reusable part 100 and the disposable part 200 constituting the dispensing patch unit 10 is by itself water tight. The sides of the parts which face the interface 19 between the parts may thus not require an additional seal (in contrast to the embodiments shown, for example, in FIGS. 4a and 4b and FIG. 7). Therefore, water sealed electrical connections 112 are provided to electrically connect the power source 203, located in the disposable part 200, with the other electrical components, such as the electronic circuitry arranged on the printed circuit board (PCB) 116, the driving mechanism 115 and the buzzer 117 that are located in the reusable part 100. The rotary wheel 114 and the driving mechanism 115 may be sealed by a flexible seal 221, which may be adjusted to match the shape of the dispensing patch unit. The flexible seal 221 may be made from material that may transfer the torque and pressure from the rotary wheel 114 to the delivery tube 210. In some embodiments, the flexible seal may be made of thermoplastic elastomer (TPE), such as fluoropolymer, polytetrafluorethylene, polyethylene, PVC and the like. Other materials may be used. In some embodiments, the seal may be relatively thin to transfer the pressure and moment from the rotary wheel 114 to the tube 210 while still providing proper sealing functionality. In some embodiments, the width of the seal may be less than 1 mm. Alternatively, the rotary wheel 114 and other components may be left out of the sealed compartment of the reusable part 100, thus providing a direct contact between the rotary wheel 114 and the delivery tube 210.

As further shown in FIGS. 11a and 11b, a vent 120 is provided in the housing 17 of the disposable part 200. In some embodiments, the vent is located in vicinity of the reservoir or the battery (or both), thus enabling pressure balancing for the reservoir 202 and provisioning of air flow to the battery 203 to be easily achieved.

The reusable part 100 may also comprise a user interface that includes one or more buttons 15 to enable manual fluid delivery programming.

Figure 12:
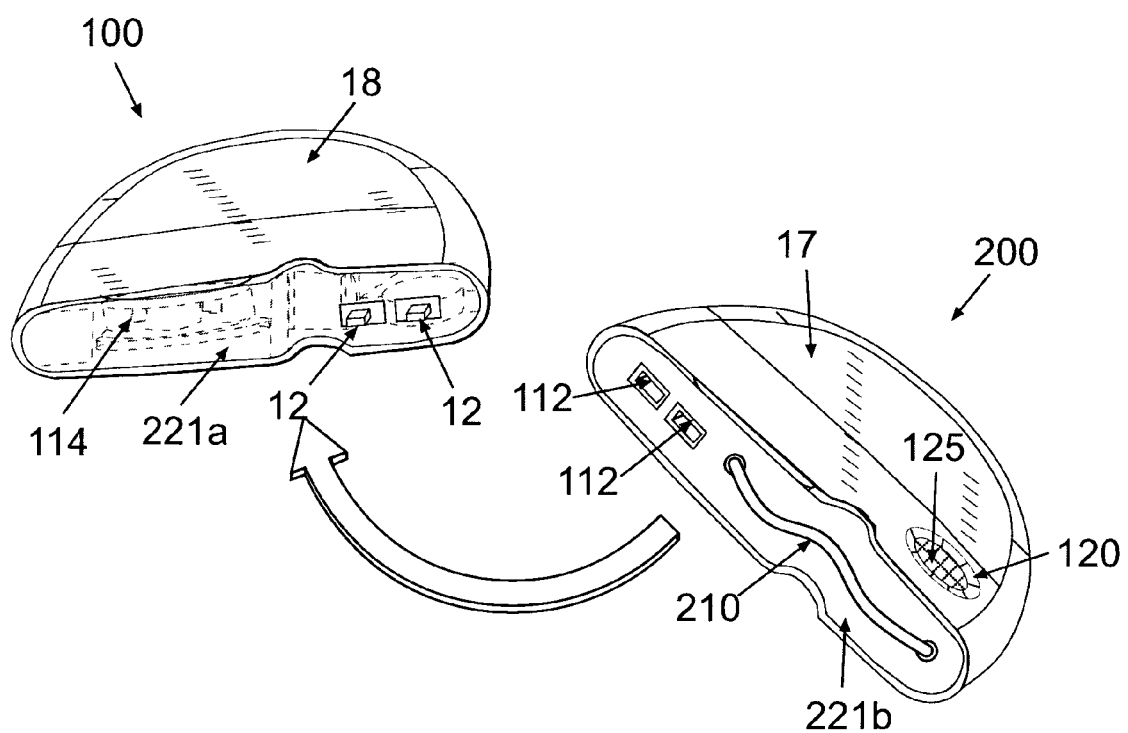
FIG. 12 is a perspective view of an exemplary a fluid dispensing device depicting the electrical and mechanical connections between a sealed reusable part and a sealed disposable part with a vent.

Referring to FIG. 12, a perspective view of an exemplary dispensing patch unit 10 is shown. A sealed reusable part 100 and a sealed disposable part 200 constitute the dispensing patch 10. A portion of the delivery tube 210 may be located outside the sealed disposable part 200 to enable better contact with the rotary wheel 114 upon attachment of the reusable part 100 to the disposable part 200. Water tight electrical connections 112 are provided to enable electrical connection with the electronic components of the dispensing patch unit. Examples of such connectors include commercially available connectors such as those manufactured by DURALINE™. Also shown are the housing 17 of the disposables part and its seal 221b, the housing 18 of the reusable part and its seal 221a, and a vent 120 located in the housing 17 covered by selectively permeable membrane 125.

Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Any and all of the foregoing patents, applications, and publications referenced in this specification are hereby incorporated by reference in their entireties. Other aspects, advantages, and modifications are considered to be within the scope of the following claims. The claims presented are representative of the inventions disclosed herein. Other, unclaimed inventions are also contemplated.

What is claimed is:

1. A fluid dispensing device for delivery of a therapeutic fluid to a user's body, the fluid dispensing device comprising:
a disposable part housing comprising at least one reservoir to hold the therapeutic fluid, and at least one other unit requiring communication with ambient air, at least partly, to operate;
a reusable part housing including at least a portion of a driving mechanism, an audible notification module disposed in the reusable part housing, and electronic components having a processor;
at least one vent port formed on one or more walls of at least one of the disposable part housing and the reusable part housing; and
a semi-permeable membrane covering the at least one vent port, the membrane being impervious to at least one liquid but pervious to at least one gas;
wherein the at least one vent port is configured for communicating air into at least one of the disposable part housing and the reusable part housing, and directing sound and/or vibration generated by the audible notification module as a notification regarding a condition of the fluid dispensing device; and wherein the at least one other unit includes a sensor to determine a body analyte level and wherein the at least one vent port is configured for providing air to the sensor to enable its operation.

2. The device of claim 1, wherein the at least one other unit includes at least one energy source comprising at least one electrochemical cell to produce electrical energy upon exposure to air.

3. The fluid dispensing device of claim 2, wherein the at least one electrochemical cell comprises a Zinc-air battery.

4. The fluid dispensing device of claim 2, wherein the reusable part housing includes the at least one vent port.

5. The fluid dispensing device of claim 1, wherein as a result of the pressure equilibrium, controlled delivery of the therapeutic fluid from the at least one reservoir to the body of the user is enabled.

6. The fluid dispensing device of claim 1, wherein the semi-permeable membrane comprises a water repelling fabric.

7. The fluid dispensing device of claim 1, wherein the semi-permeable membrane comprises a polymer.

8. The fluid dispensing device of claim 1, wherein the semi-permeable membrane comprises GORE-TEX®.

9. The fluid dispensing device of claim 1, wherein the semi-permeable membrane comprises CELGARD®.

10. The fluid dispensing device of claim 1, wherein the semi-permeable membrane is configured to provide a rate of gas transfer greater than or equal to about 0.1 micro-liter per hour at a temperature of about 300° K and pressure conditions of about 1 atm.

11. The fluid dispensing device of claim 1, wherein the semi-permeable membrane is configured to provide a rate of gas transfer greater than or equal to about 2.5 micro liter per second at a temperature of about 300° K and pressure conditions of about 1 atm.

12. The fluid dispensing device of claim 1, wherein the disposable part housing and the reusable part housing are substantially sealed when operatively coupled to each other, and wherein at least one of the disposable part housing and the reusable part housing allow ingress of liquids when not operatively coupled to the other part.

13. The fluid dispensing device of claim 1, further comprising at least one seal to substantially close the at least one vent port to prevent entry of air into the disposable part housing and/or the reusable part housing through the at least one vent port when the device is not in operation.

14. The fluid dispensing device of claim 1, wherein the at least one vent port is configured for communicating air into at least one of the disposable part housing and the reusable part housing to maintain pressure equilibrium between the air pressure therein and the ambient air pressure thereout, and provide communication with the ambient air to the at least one other unit requiring air to enable operation of the at least one other unit.

15. A fluid dispensing device for delivery of a therapeutic fluid to a user's body, the fluid dispensing device comprising:
 a disposable part housing comprising at least one reservoir to hold the therapeutic fluid, at least one sensor to determine a body analyte level, and at least one energy source comprising at least one Zinc-air battery which provides energy upon exposure to air;
 a reusable part housing including at least a portion of a driving mechanism and electronic components having a processor, wherein the disposable part housing and the reusable part housing are substantially sealed when operatively coupled to each other, and wherein at least one of the disposable part housing and the reusable part housing allows ingress of liquids when not operatively coupled to the other part;
 at least one vent port formed on one or more walls of at least one of the disposable part housing and the reusable part housing;
 a semi-permeable membrane comprising a water-repelling fabric which substantially covers and/or is provided at the at least one vent port, the membrane being impervious to at least one liquid but pervious to at least one gas;
 wherein the at least one vent port is configured for communicating air into at least one of the disposable part housing and the reusable part housing to at least one of:
  maintain pressure equilibrium between the air pressure therein and the ambient air pressure thereout, and
  provide communication with the ambient air to the at least one Zinc-air battery and, to the at least one sensor to enable operation of the at least one Zinc-air battery and the at least one sensor,
 and wherein as a result of the pressure equilibrium, controlled delivery of the therapeutic fluid from the at least one reservoir to the body of the user is enabled;
 and
 an audible notification module disposed in the reusable part housing, wherein the at least one vent port is further configured to direct sound and/or vibration generated by the audible notification module as a notification regarding a condition of the fluid dispensing device.

16. A method for delivery of a therapeutic fluid to a user's body using a fluid dispensing device, comprising:
 providing a fluid dispensing device comprising:
  a disposable part housing comprising at least one reservoir to hold the therapeutic fluid, at least one sensor to determine a body analyte level, and at least one energy source comprising at least one Zinc-air battery which provides energy upon exposure to air;
  a reusable part housing including at least a portion of a driving mechanism, an audio notification module, and electronic components having a processor;
  at least one vent port formed, on one or more walls of at least one of the disposable part housing and the reusable part housing;
  a semi-permeable membrane which substantially covers and/or is provided at the at least one vent port, the membrane being impervious to at least one liquid but pervious to at least one gas,
  wherein the at least one vent port is configured for communicating air into at least one of the disposable part housing and the reusable part housing to at least one of:
   maintain pressure equilibrium between the air pressure therein and the ambient air pressure there out, and
   provide communication with the ambient air to the at least one Zinc air battery requiring air and to the at least one sensor to enable operation of the at least one Zinc air battery and the at least one sensor, and
  wherein the at least one vent port is further configured to direct sound and/or vibration generated by the audible notification module as a notification regarding a condition of the fluid dispensing device;
 operatively coupling the disposable part housing and the reusable part housing together, wherein as a result of such coupling:
  the disposable part housing and the reusable part housing are substantially sealed, ambient air flow is established to the Zinc-air battery enabling operation of the fluid dispensing device, and therapeutic fluid is provided to the user.

* * * * *

UNITED STATES PATENT AND TRADEMARK OFFICE
CERTIFICATE OF CORRECTION

PATENT NO.        : 8,491,529 B2
APPLICATION NO. : 12/452764
DATED             : July 23, 2013
INVENTOR(S)       : Yodfat et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 408 days.

Signed and Sealed this
Eighth Day of September, 2015

Michelle K. Lee
*Director of the United States Patent and Trademark Office*